United States Patent [19]

Gustavson et al.

[11] Patent Number: 5,783,171
[45] Date of Patent: Jul. 21, 1998

[54] RADIONUCLIDE METAL $N_2S_2$ CHELATES SUBSTITUTED WITH GLUCOSE AND BIOTIN MOIETIES

[75] Inventors: Linda M. Gustavson, Seattle; Sudhakar Kasina, Mercer Island; Alan R. Fritzberg, Edmonds, all of Wash.

[73] Assignee: NeoRx Corporation, Seattle, Wash.

[21] Appl. No.: 591,560

[22] PCT Filed: Jul. 12, 1994

[86] PCT No.: PCT/US94/07733

§ 371 Date: Mar. 11, 1996

§ 102(e) Date: Mar. 11, 1996

[87] PCT Pub. No.: WO95/02418

PCT Pub. Date: Jan. 26, 1995

Related U.S. Application Data

[63] Continuation of Ser. No. 90,421, Jul. 12, 1993, abandoned, which is a continuation-in-part of Ser. No. 973,048, Nov. 6, 1992, Pat. No. 5,250,666, which is a division of Ser. No. 577,959, Sep. 5, 1990, Pat. No. 5,164,176, which is a continuation-in-part of Ser. No. 367,502, Jun. 16, 1989, abandoned.

[51] Int. Cl.[6] .............. A61K 51/00; C07F 5/00; C07D 235/02

[52] U.S. Cl. .............. 424/1.73; 424/1.65; 424/1.69; 534/10; 534/13; 534/14; 548/303.7; 548/304.1

[58] Field of Search .............. 534/10, 14, 13; 424/1.65, 1.77, 9.364, 9.365, 9.36, 1.69, 1.73; 536/17.1, 17.2; 548/303.7, 304.1; 564/154

[56] References Cited

U.S. PATENT DOCUMENTS

| | | | |
|---|---|---|---|
| 5,021,556 | 6/1991 | Srinivasan | 534/10 |
| 5,175,343 | 12/1992 | Fritzberg et al. | 560/145 |
| 5,283,342 | 2/1994 | Gustavson et al. | 548/304.1 |
| 5,422,095 | 6/1995 | Hashiguchi et al. | 424/1.73 |
| 5,541,287 | 7/1996 | Yau et al. | 530/317 |
| 5,578,287 | 11/1996 | Theodore et al. | 424/1.49 |

*Primary Examiner*—Gary E. Hollinden
*Assistant Examiner*—Michael G. Hartley
*Attorney, Agent, or Firm*—Seed and Berry LLP

[57] ABSTRACT

Chelating compounds of specified structure are useful for radiolabeling targeting proteins such as antibodies as well as proteinaceous and non-proteinaceous ligands and anti-ligands. The radiolabeled antibodies, ligands or anti-ligands, or catabolites thereof, demonstrate improved biodistribution properties, including reduced localization within the intestines.

13 Claims, 8 Drawing Sheets

Synthesis of succinate reagent 16 via oxathiolone

Synthesis of succinate reagent 16 using LDA

RADIONUCLIDE METAL $N_2S_2$ CHELATES SUBSTITUTED WITH GLUCOSE AND BIOTIN MOIETIES

CROSS REFERENCE TO RELATED APPLICATIONS

This application is a 371 of PCT/US94/07733, filed Jul. 12, 1994, which is a continuation of U.S. Ser. No. 08/090,421, filed Jul. 12, 1993, now abandoned; which is a continuation-in-part of U.S. Ser. No. 07/973,048, filed Nov. 6, 1992, U.S. Pat. No. 5,250,666; which is a divisional of U.S. Ser. No. 07/577,959, filed Sep. 5, 1990, U.S. Pat. No. 5,164,176; which is a continuation-in-part of U.S. Ser. No. 07/367,502, filed on Jun. 16, 1989, now abandoned.

BACKGROUND

Radiolabeled antibodies are used in a variety of diagnostic and therapeutic medical procedures. The increased specificity of monoclonal antibodies, compared to polyclonal antibodies, makes them even more useful for delivering diagnostic or therapeutic agents such as radioisotopes to desired target sites in vivo. A monoclonal antibody specific for a desired type of target cells such as tumor cells may be used to deliver a therapeutic radionuclide attached to the antibody to the target cells, thereby causing the eradication of the undesired target cells. Alternatively, a monoclonal antibody having a diagnostically effective radionuclide attached thereto may be administered, whereupon the radiolabeled antibody localizes on the target tissue. Conventional diagnostic procedures then may be used to detect the presence of the target sites within the patient. In contrast to such "chelate-labeled antibody" procedures, pretargeting approaches may be used to achieve therapeutic or diagnostic goals, which pretargeting approaches involve the interaction of two members of a high affinity binding pair such as a ligand-anti-ligand binding pair.

One method for radiolabeling proteins such as antibodies as well as proteinaceous and non-proteinaceous binding pair members involves attachment of radionuclide metal chelates to the proteins or binding pair members. Chelates having a variety of chemical structures have been developed for this purpose. The usefulness of such chelates is dependent upon a number of factors such as the stability of radionuclide binding within the chelate and the reactivity of the a chelate with the desired protein or binding pair member. The efficiency of radiolabeling of the chelating compound to produce the desired radionuclide metal chelate also is important. Another consideration is the biodistribution of the radiolabeled antibody or binding pair member and catabolites thereof in vivo. Localization in non-target tissues limits the total dosage of a therapeutic radiolabeled antibody or binding pair member that can be administered, thereby decreasing the therapeutic effect. In diagnostic procedures, localization in non-target tissues may cause undesirable background and/or result in misdiagnosis. The need remains for improvement in these and other characteristics of radionuclide metal chelate compounds used for radiolabeling of proteins such as antibodies. The use of pretargeting approaches diminishes non-target tissue localization of radiolabel; however, the need remains for improvement in molecules incorporating chelates and binding pair members of proteinaceous or non-proteinaceous structure.

SUMMARY OF THE INVENTION

The present invention provides a compound of the formula:

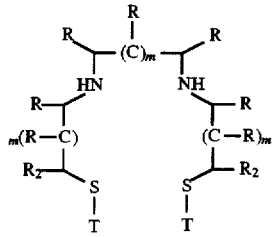

wherein:

each R independently represents =O, $H_2$, a lower alkyl group, —$(CH_2)_n$—COOH, —$(CH_2)_n$—CO-saccharide or saccharide derivative, or —$(CH_2)_n$—NH-saccharide or saccharide derivative, or $R_1$—Z;

n is 0 to about 3;

$R_1$ represents a lower alkyl or substituted lower alkyl group;

Z represents a protein conjugation group, a ligand conjugation group, an anti-ligand conjugation group or a targeting protein, ligand or anti-ligand; or a ligand-linker moiety or an anti-ligand-linker moiety wherein the linker moiety is derived from a ligand or anti-ligand conjugation group;

each $R_2$ independently represents $H_2$, a lower alkyl group, —$(CH_2)_n$—COOH, —$(CH_2)_n$—CO-saccharide or saccharide derivative, or —$(CH_2)_n$—NH-saccharide or saccharide derivative, or $R_1$—Z;

each m is 0 or 1, with at most one m=1;

each T represents a sulfur protecting group; and the compound comprises at least one $(CH_2)_n$—COOH substituent or one —$(CH_2)_n$—CO-saccharide or saccharide derivative or —$(CH_2)_n$—NH-saccharide or saccharide derivative substituted and one —$R_1$—Z substituent.

The present invention also provides radionuclide metal chelate compounds of the formula:

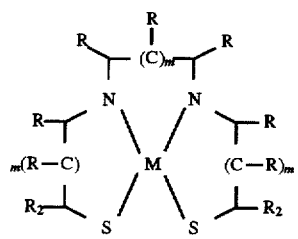

wherein:

M represents a radionuclide metal or oxide thereof and the other symbols are as described above.

These compounds comprise a targeting protein such as an antibody, or a conjugation group for attachment of the compound to a targeting protein. Alternatively, the compounds include a ligand or an anti-ligand or a conjugation group for the attachment of the compound to a ligand or to an anti-ligand. The chelating compound may be attached to a targeting protein, ligand or anti-ligand and subsequently radiolabeled. Alternatively, the radionuclide metal chelate compound may be prepared and then attached to a targeting protein, ligand or anti-ligand. The resulting radiolabeled targeting proteins, ligands or anti-ligands are useful in diagnostic and therapeutic medical procedures. An example of a targeting protein is a monoclonal antibody that binds to cancer cells. An example of a ligand is biotin, with the complementary anti-ligand thereof being avidin or streptavidin, wherein biotin and avidin or streptavidin together form a ligand-anti-ligand binding pair.

Some additional compounds of the present invention incorporate an ester cleavable $R_1$ moiety exhibiting, for example, ester and/or amide functionalities. An example of a chelate-biotin conjugate of this aspect of the present invention, involving a succinate mono-ester mono-amide, is shown below:

the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Anti-ligands of the present invention may exhibit or be derivitized to exhibit structural features that direct the uptake thereof, e.g., galactose residues that direct liver uptake. Avidin and streptavidin are used herein as prototypical anti-ligands.

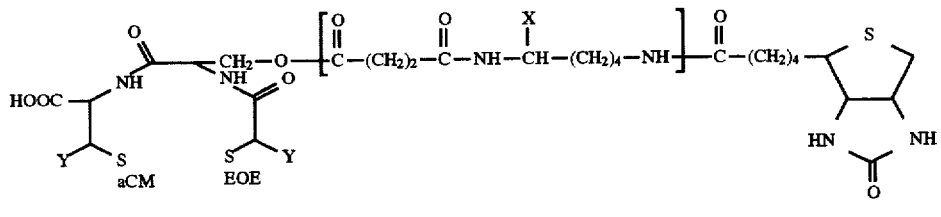

Each Y = H or CH₂COOH wherein X is H or COOH.

The carboxylic acid substituent(s) on the compounds of the present invention are believed to assist in chelation of a radionuclide and to contribute to improved biodistribution properties of catabolites of the radiolabeled targeting proteins, ligands or anti-ligands. Reduced localization of radioactivity within the intestines is achieved using the radiolabeled targeting proteins, ligands or anti-ligands of the present invention.

DETAILED DESCRIPTION OF THE INVENTION

Figure 1:
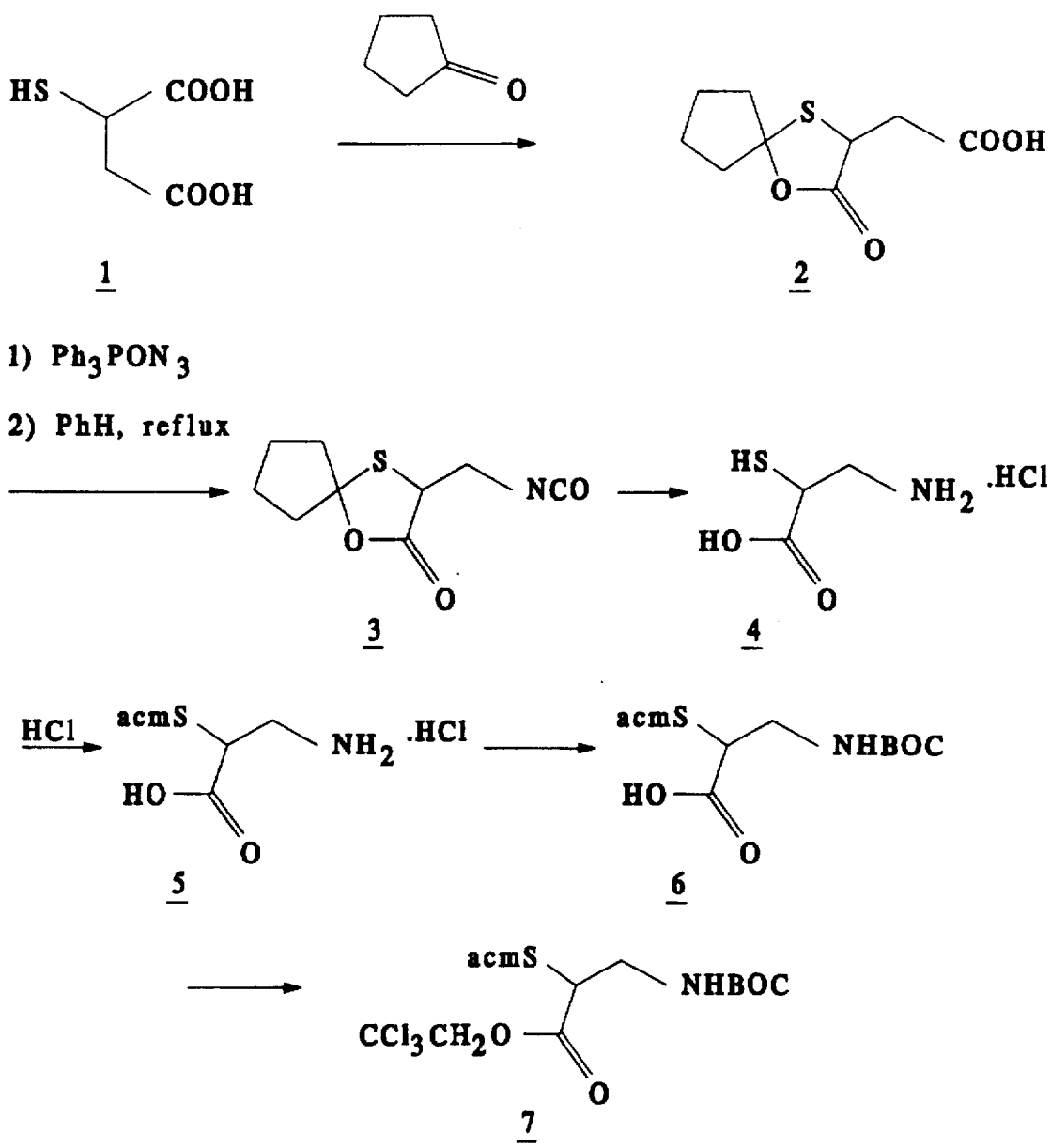
FIGS. 1–7 depict chemical synthesis procedures that may be used to prepare certain chelating compounds of the present invention.

Prior to setting forth the invention, it may be helpful to set forth definitions of certain terms to be used within the disclosure.

Targeting moiety: A molecule that binds to a defined population of cells. The targeting moiety may bind a receptor, an oligonucleotide, an enzymatic substrate, an antigenic determinant, or other binding site present on or in the target cell population. Targeting moieties that are proteins are referred to herein as "targeting proteins." Antibody is used throughout the specification as a prototypical example of a targeting moiety and a targeting protein. Tumor is used as a prototypical example of a target in describing the present invention.

Ligand/anti-ligand pair: A complementary/anticomplementary set of molecules that demonstrate specific binding, generally of relatively high affinity. Exemplary ligand/anti-ligand pairs include zinc finger protein/dsDNA fragment, hapten/antibody, lectin/carbohydrate, ligand/receptor, and biotin/avidin. Biotin/avidin is used throughout the specification as a prototypical example of a ligand/anti-ligand pair.

Anti-ligand: As defined herein, an "anti-ligand" demonstrates high affinity, and preferably, multivalent binding of Avidin and Streptavidin: As defined herein, both of the terms "avidin" and "streptavidin" include avidin, streptavidin and derivatives and analogs thereof that are capable of high affinity, multivalent or univalent binding of biotin.

Ligand: As defined herein, a "ligand" is a relatively small, soluble molecule that exhibits rapid serum, blood and/or whole body clearance when administered intravenously in an animal or human. Biotin is used as the prototypical ligand.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step and other related methods described herein are also encompassed.

Linker Moiety: A moiety that is a portion of a protein, ligand or anti-ligand conjugation group that remains part of the structure of a protein-chelate, ligand-chelate or anti-ligand-chelate conjugate following the conjugation step. For example, the linker moiety of an active ester chelate derivative includes, for example, a carbonyl (—CO—) moiety.

The present invention provides chelating compounds and radionuclide metal chelate compounds prepared therefrom, as well as radiolabeled proteins, ligands or anti-ligands having the chelates attached thereto. The radionuclide metal chelates of the present invention are attached to targeting proteins such as antibodies to form radiolabeled targeting proteins having diagnostic or therapeutic use. The compounds each comprise a targeting protein or a protein conjugation group for attachment of the compound to a targeting protein. Alternatively, the radionuclide metal chelates of the present invention are attached to ligands or anti-ligands to form radiolabeled ligands or anti-ligands having diagnostic or therapeutic use. Such compounds include a ligand or anti-ligand conjugation group to facilitate attachment of the compound to a ligand or anti-ligand. The compounds also comprise at least one carboxylic acid substituent. The good radiolabeling yields (i.e., chelate formation) achieved with these compounds are believed to be attributable, at least in part, to the presence of the carboxylic acid substituent(s). The improved biodistribution properties of the radiolabeled proteins of the invention also are believed to be at least in part attributable to the carboxylic acid substituent(s) on the chelate.

Provided by the present invention are chelating compounds of the following formula:

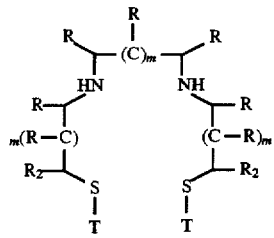

wherein:

each R independently represents =O, H$_2$, a lower alkyl group, —(CH$_2$)$_n$—COOH, —(CH$_2$)$_n$—CO-saccharide or saccharide derivative, or —(CH$_2$)$_n$—NH-saccharide or saccharide derivative, or R$_1$—Z;

n is 0 to 3;

R$_1$ represents a lower alkyl or substituted lower alkyl group;

Z represents a protein conjugation group, a ligand conjugation group, an anti-ligand conjugation group or a targeting protein, ligand or anti-ligand; or a ligand-linker moiety or an anti-ligand-linker moiety wherein the linker moiety is derived from a ligand or an anti-ligand conjugation group;

each R$_2$ independently represents H$_2$, a lower alkyl group, —(CH$_2$)$_n$—COOH, —(CH$_2$)$_n$—CO-saccharide or saccharide derivative, or —(CH$_2$)$_n$—NH-saccharide or saccharide derivative, or R$_1$—Z;

each m is 0 or 1, with at most one m=1;

each T represents a sulfur protecting group; and the compound comprises at least one —(CH$_2$)$_n$—COOH substituent —(CH$_2$)$_n$—CO-saccharide or saccharide derivative, or —(CH$_2$)$_n$—NH-saccharide or saccharide derivative substituent and one —R$_1$—Z substituent.

The above presented chelating compounds are radiolabeled to form the corresponding radionuclide metal chelates of the following formula:

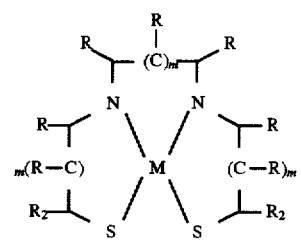

wherein:

M represents a radionuclide metal or an oxide thereof and all the other symbols are as described above.

Some additional compounds of the present invention incorporate ester cleavable R$_1$ moieties, incorporating, for example, ester and/or amide-containing R$_1$ groups. An example of such compounds of the present invention employing a cleavable succinate mono-ester mono-amide linkage has the formula shown below:

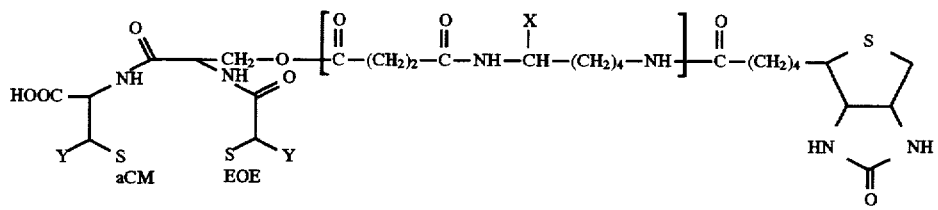

Each Y = H or CH$_2$COOH wherein X is H or COOH. The advantage of an ester cleavable R$_1$ group is a reduction in non-target cell retention. Also, ester functionalities often improve water solubility and overall polarity of small molecules. Preparation of compounds having ester cleavable linkers is discussed in the Examples set forth below.

A protein conjugation group is a chemically reactive functional group that will react with a protein under conditions that do not denature or otherwise adversely affect the protein. The protein conjugation group therefore is sufficiently reactive with a functional group on a protein so that the reaction can be conducted in substantially aqueous solutions and does not have to be forced, e.g. by heating to high temperatures, which may denature the protein. Examples of suitable protein conjugation groups include but are not limited to active esters, isothiocyanates, amines, hydrazines, thiols, and maleimides. Among the preferred active esters are thiophenyl ester, 2,3,5,6-tetrafluorophenyl ester, and 2,3,5,6-tetrafluorothiophenyl ester. The preferred active esters may comprise a group that enhances water solubility, at the para (i.e., 4) position on the phenyl ring. Examples of such groups are CO$_2$H, SO$_3^-$, PO$_3^{2-}$ and OPO$_3^{2-}$, and O(CH$_2$CH$_2$O)$_n$CH$_3$ groups.

A ligand or anti-ligand conjugation group is a chemically reactive functional group that will react with a ligand or anti-ligand under conditions that do not adversely affect the ligand or anti-ligand, including the capacity of the ligand or anti-ligand to bind to its complementary binding pair member. Ligand or anti-ligand conjugation groups therefore are sufficiently reactive with a functional group on a ligand or anti-ligand so that the reaction can be conducted under relatively mild reaction conditions including those described above for protein-chelate conjugation. For proteinaceous ligands or anti-ligands, such as streptavidin, protein conjugation groups may correspond to ligand or anti-ligand conjugation groups. Examples of suitable ligand or anti-ligand conjugation groups therefore include, but are not limited to, active esters, isothiocyanates, amines, hydrazines, thiols, and maleimides. Among the preferred active esters are thiophenyl ester, 2,3,5,6-tetrafluorophenyl ester, and 2,3,5,6-tetrafluorothiophenyl ester. The preferred active esters may comprise a group that enhances water solubility, at the para (i.e., 4) position on the phenyl ring. Examples of such groups are $CO_2H$, $SO_3^-$, $PO_3^{2-}$, $OPO_3^{2-}$, and $O(CH_2CH_2O)_nCH_3$ groups.

For non-proteinaceous ligand or anti-ligand moieties, such as biotin, suitable conjugations groups are those functional groups that react with a ligand or anti-ligand functional group (e.g., a terminal carboxy group) or a functional group which the ligand or anti-ligand has been derivatized to contain (e.g., an alcohol or an amine group produced by the reduction of a terminal carboxy moiety). As a result, conjugation groups, such as those recited above, that are capable of reacting with —COOH, —OH or —NH$_2$ groups are useful conjugation groups for producing biotin-chelate molecules of this aspect of the present invention. Exemplary biotin-COOH conjugation groups are amines, hydrazines, alcohols and the like. Exemplary biotin-OH conjugation groups are tosylates (Ts), active esters, halides and the like, with exemplary groups being reactive with biotin-O-Ts including amines, hydrazines, thiols and the like. Exemplary biotin-NH$_2$ conjugation groups are active esters, acyl chlorides, tosylates, isothiocyanates and the like.

The protein conjugation group, ligand conjugation group, or anti-ligand conjugation group (represented as Z in the above-presented formulas) is attached to the chelating compound core through the linkage represented as $R_1$. $R_1$ is a lower alkyl or substituted lower alkyl group. By "lower alkyl" is meant an alkyl group of preferably one to four carbon atoms. Most preferably, $R_1$ is a methylene chain comprising from two to three carbon atoms. The lower alkyl group may be substituted with hetero atoms such as oxygen or nitrogen atoms. When the protein conjugation group, ligand conjugation group, or anti-ligand conjugation group is a primary amine, the $R_1$ linkage comprises a methylene group immediately adjacent to the terminal primary amine protein conjugation group.

The "targeting moiety" of the present invention binds to a defined target cell population, such as tumor cells. Preferred targeting moieties useful in this regard include antibody and antibody fragments, proteinaceous or non-proteinaceous ligands or anti-ligands, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a mimetic compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

The term "targeting protein" as used herein refers to proteins which are capable of binding to a desired target site in vivo. The targeting protein may bind to a receptor, substrate, antigenic determinant, complementary binding pair member or other binding site on a target cell or other target site. The targeting protein serves to deliver the radionuclide attached thereto to the desired target site in vivo. Examples of targeting proteins include, but are not limited to, antibodies and antibody fragments, proteinaceous ligands or anti-ligands, hormones, fibrinolytic enzymes, and biologic response modifiers. The term "targeting protein" includes proteins, polypeptides, and fragments thereof. In addition, other molecules that localize in a desired target site in vivo, although not strictly proteins, are included within the definition of the term "targeting proteins" as used herein. For example, certain carbohydrates or glycoproteins may be used in the present invention. The proteins may be modified, e.g., to produce variants and fragments thereof, as long as the desired biological property (i.e., the ability to bind to the target site) is retained. The proteins may be modified by using various genetic engineering or protein engineering techniques.

Among the preferred targeting proteins are antibodies, most preferably monoclonal antibodies. A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05 to the 250 kilodalton human melanoma-associated proteoglycan; and NR-LU-10 to a pancarcinoma glycoprotein. The antibody employed in the present invention may be an intact (whole) molecule, a fragment thereof, or a functional equivalent thereof. Examples of antibody fragments are F(ab')$_2$, Fab', Fab, and F$_v$ fragments, which may be produced by conventional methods or by genetic or protein engineering.

Human monoclonal antibodies or "humanized" murine antibodies are also useful as targeting moieties in accordance with the present invention. For example, murine monoclonal antibody may be "humanized" by genetically recombining the nucleotide sequence encoding the murine Fv region (i.e., containing the antigen binding site) or the complementarity determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

Targeting proteins are rarely completely specific for a desired target site. Localization in non-target tissues may occur through cross-reactivity or non-specific uptake, for example. In the case of radiolabeled targeting proteins, such localization at non-target sites may result in decreased clarity of diagnostic images (due to the increased "background") and misdiagnosis. Exposure of non-target tissues to radiation also occurs, which is especially undesirable in therapeutic procedures. The improved biodistribution properties of the radiolabeled targeting proteins of the present invention are believed to be attributable to the effect of the chelate, most likely on the biodistribution of catabolites of the radiolabeled proteins.

Ligands suitable for use within the present invention include biotin, haptens, lectins, epitopes, dsDNA fragments and analogs and derivatives thereof. Useful complementary anti-ligands include avidin (for biotin), carbohydrates (for lectins), antibody, fragments or analogs thereof, including mimetics (for haptens and epitopes) and zinc finger proteins (for dsDNA fragments). Preferred ligands and anti-ligands bind to each other with an affinity of at least about $k_D \geq 10^{-9}$M.

The chelating compounds of the present invention comprise two nitrogen and two sulfur donor atoms, and thus may be termed "$N_2S_2$" chelating compounds. The radiolabeled targeting proteins of the present invention exhibit certain improved biodistribution properties compared to targeting proteins radiolabeled with certain other $N_2S_2$ chelates. Most notably, localization of radiolabeled targeting proteins (or catabolites thereof) within the intestines is reduced.

Targeting proteins radiolabeled with certain $N_2S_2$ radionuclide metal chelates are described, for example, in European Patent Application Publication Number 188,256. When the radiolabeled proteins of EP 188,256 are administered in vivo, a percentage of the injected dosage of the radionuclide becomes localized within the intestines (i.e., becomes part of the intestinal contents, rather than binding to intestinal epithelial tissue per se). Although stable attachment of radionuclides to antibodies and effective localization thereof on target tumors has been achieved using the EP 188,256 system, reduction of the intestinal localization would be beneficial. A portion of the non-target-bound administered radiolabeled proteins (e.g., antibodies or fragments thereof) most likely is first metabolized to produce radiolabeled catabolites that subsequently enter the intestines, probably through hepatobiliary excretion. When the chelate is attached to lysine residues of the targeting protein, a major catabolite may be the lysine adduct of the chelate. Intestinal localization of radioactivity may be confused with (or obstruct) target sites in the abdominal area. For therapeutic procedures, the dosage that can be safely administered is reduced when intestinal localization occurs (due to exposure of normal tissues to the radiation). The therapeutic effect on the target sites therefore also is reduced.

As illustrated in the examples below, the biodistribution patterns in vivo differ when targeting proteins (e.g., antibody fragments) are radiolabeled with a chelate of the present invention, compared to radiolabeling using certain other $N_2S_2$ chelates. The advantage of reduced intestinal localization is demonstrated for the radiolabeled targeting proteins of the present invention. While not wishing to be bound by theory, it is believed that the carboxylic acid substituent(s) on the chelate confer the advantageous biodistribution properties on catabolites of the radiolabeled protein (most likely lysine adducts of the chelate). The carboxylic acid substituent(s) on the compounds of the present invention increase the polarity, and therefore the water solubility, of the compounds. The increased water solubility is believed to promote excretion of the catabolites by the kidneys, resulting in efficient elimination of the radioactive catabolites in the urine. Other substituents that enhance polarity (e.g., sulfate groups) may be used on the chelating compounds, in addition to (or instead of) the COOH substituents.

Another advantage of the chelates of the present invention is the comparatively good radiolabeling yields. The free carboxylic acid substituent(s) are believed to assist in the chelation of the radionuclide. Radiolabeled ligands and anti-ligands also exhibit these favorable biodistribution and chelation properties.

During radiolabeling, bonds form between the four donor atoms and the radionuclide metal to form the corresponding radionuclide metal chelate. Any suitable conventional sulfur protecting group(s) may be attached to the sulfur donor atoms of the compounds of the present invention. The protecting groups should be removable, either prior to or during the radiolabeling reaction. The protecting groups attached to the two sulfur donor atoms may be the same or different. Alternatively, a single protecting group, e.g. a thioacetal group, may protect both sulfur donor atoms. Among the preferred sulfur protecting groups are acetamidomethyl and hemithioacetal protecting groups, which are displacable from the chelating compound during the radiolabeling reaction. Preferably, at least one sulfur protecting group is a hemithioacetal group, and at most one sulfur protecting group is an acetamidomethyl group.

An acetamidomethyl sulfur-protecting group is represented by the following formula, wherein the sulfur atom shown is a sulfur donor atom of the chelating compound:

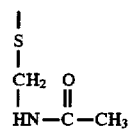

The acetamidomethyl group is displaced from the chelating compound during radiolabeling conducted at about 50° C. in a reaction mixture having a pH of about 3 to 6.

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

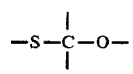

Preferred hemithioacetals generally are of the following formula, wherein the sulfur atom is a sulfur atom of the chelating compound, and a separate protecting group is attached to each of the sulfur atoms on the chelating compound:

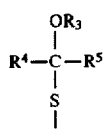

wherein $R^3$ is a lower alkyl group, preferably of from two to five carbon atoms, and $R^4$ is a lower alkyl group, preferably of from one to three carbon atoms. Alternatively, $R^3$ and $R^4$ may be taken together with the carbon atom and the oxygen atom shown in the formula to define a nonaromatic ring, preferably comprising from three to seven carbon atoms in addition to the carbon and oxygen atoms shown in the formula. $R^5$ represents hydrogen or a lower alkyl group wherein the alkyl group preferably is of from one to three carbon atoms. Examples of such preferred hemithioacetals include, but are not limited to:

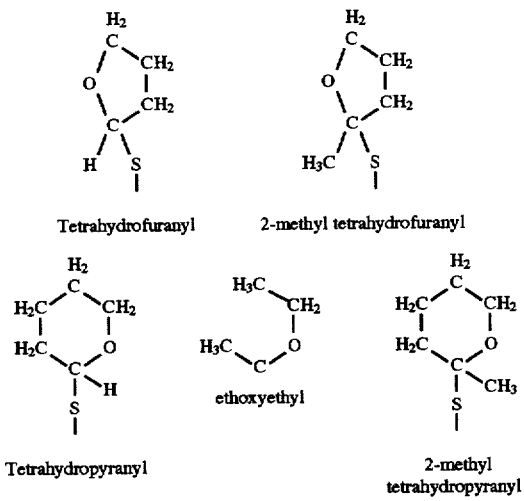

These sulfur-protective groups are displaced during the radiolabeling reaction, conducted at acidic pH, in what is believed to be metal-assisted acid cleavage. Covalent bonds form between the sulfur atoms and the metal radionuclide. A separate step for removal of the sulfur-protective groups is not necessary. The radiolabeling procedure thus is simplified. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or otherwise adversely affected by exposure to basic pH. In general, such groups include esters, maleimides, and isothiocyanates, among others. Such groups may be present on the chelating compounds as protein, ligand or anti-ligand conjugation groups.

The compounds of the present invention preferably comprise at least one =O substituent, most preferably two =O substituents. In one embodiment of the invention at least one and preferably two $R_2$ substituents are —$(CH_2)_n$—COOH, with n preferably equal to 1.

Examples of the chelating compounds of the present invention are the compounds of the following formulas:

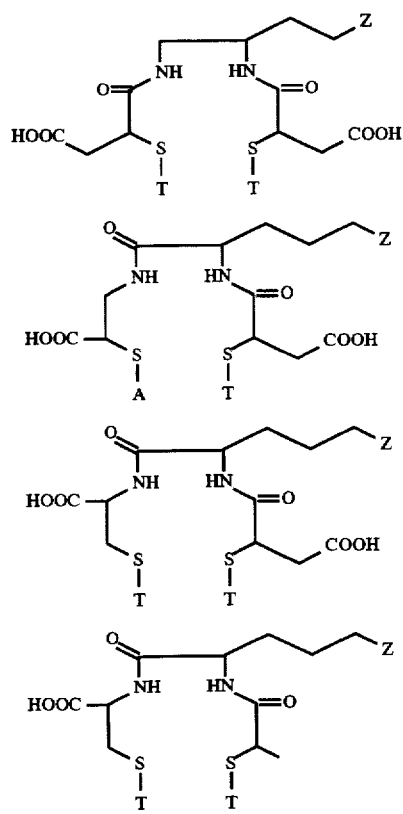

wherein the symbols are as described above. Procedures for synthesizing these compounds are presented in the examples below. In one embodiment of the invention, these chelating compounds comprise either two hemithioacetal, or one hemithioacetal and one acetamidomethyl sulfur protecting groups.

Other chelating compounds of the present invention incorporate one or more saccharide residues. A preferred number of saccharide residues ranges from 1 to about 10, although when polymeric saccharides are employed the number of saccharide residues therein may be higher.

Saccharides, such as hexoses (e.g., glucose) and pentoses (e.g., fructose) and polymers of such saccharides are hydrophilic and, consequently, are generally excreted efficiently into the urine by glomular filtration. Inulin, a 5 kD polymer of fructose, is the gold standard for glomular filtration studies. Derivatization of a chelating compound with one or more hexose residues, such as glucose residues, for example, is expected to increase the water solubility and hydrophilicity of the chelating compound and conjugates containing the same. Consequently, glucose-bearing chelating compounds and conjugates will exhibit enhanced renal excretion.

Saccharide or saccharide derivative-bearing conjugates can be prepared in accordance with procedures discussed in the examples below for glucose derivative-bearing conjugates. Exemplary glucose derivative-containing conjugates of the present invention can be prepared from a variety of intermediates including glucose, glucosamine, gluconate, glucoheptonate, gluconic acid, gluconolactone, glucaric acid (i.e., saccharic acid), D-saccharic 1,4-lactone monohydrate, glucuronic acid, and the like, other sugars and sugar derivatives of similar functionalization are also commercially available and useful in the practice of the present invention.

The choice of sugar derivative (unmodified, amino functionalized or carboxy functionalized) depends on the conjugating group of the chelating compound. For example, amino sugars are preferred for conjugation to chelating compound carboxyl groups. Glucosamine, for example, is useful for this purpose, as it allows amino group reaction with appropriate derivatives of chelating compounds such as active esters, active halides, aldehydes.

Alternatively, saccharide compounds bearing carboxyl residues are commercially available and can be reacted with amine derivatives of chelating compounds. Glucuronic acid, for example, is useful for this purpose, as it bears a carboxy residue available for reaction with a chelating compound amine.

Also, native saccharide compounds, such as glucose for example, can be reacted with chelating compound amines to form amine-linked sugar-chelating compound conjugates. Subsequent or concurrent imine reduction results in a stable amine linkage.

Sugar lactones may be employed in the preparation of amide-linked sugar-chelating compound conjugates. The lactone serves as an activated carboxylic acid which undergoes nucleophilic, ring opening upon reaction with amine bearing chelating compounds.

The following table summarizes examples of saccharide (sugar)-chelating compound (non-sugar) chemical conjugates prepared via nucleophile-electrophile reaction:

| Nucleophile | Electrophile | Sugar Derivative | Linkage |
|---|---|---|---|
| sugar amine | activated carboxyl | glucosamine | amide |
| amino | sugar aldehyde | native sugar | amine |
| amino | activated sugar carboxyl | glucuronic acid | amide |
| amino | sugar lactone | gluconolactone | amide |
| hydrazide | sugar aldehyde | native sugar | hydrazide |

The chelating compounds of the present invention are radiolabeled, using conventional procedures, with any of a variety of radionuclide metals to form the corresponding radionuclide metal chelates. These radionuclide metals include, but are not limited to, copper (e.g., $^{67}$Cu and $^{64}$Cu); technetium (e.g., $^{99m}$Tc); rhenium (e.g., $^{186}$Re and $^{188}$Re); lead (e.g., $^{212}$Pb); bismuth (e.g, $^{212}$Bi); and palladium (e.g., $^{109}$Pd). Methods for preparing these isotopes are known. Molybdenum/technetium generators for producing $^{99m}$Tc are commercially available. Procedures for producing $^{186}$Re include the procedures described by Deutsch et al., (*Nucl. Med. Biol.*, Vol. 13:4:465–477, 1986) and Vanderheyden et al. (*Inorganic Chemistry*, Vol. 24:1666–1673, 1985), and methods for production of $^{188}$Re have been described by Blachot et al. (*Intl. J. of Applied Radiation and Isotopes*, Vol. 20:467–470, 1969) and by Klofutar et al. (*J. of Radioanalytical Chem.*, Vol. 5:3–10, 1970). Production of $^{212}$Pd is described in Fawwaz et al., *J. Nucl. Med.* (1984), 25:796. Production of $^{212}$Pb and $^{212}$Bi is described in Gansow et al., *Amer. Chem. Soc. Symp. Ser.* (1984), 241:215–217, and Kozah et al., *Proc. Nat'l. Acad. Sci. USA* (January 1986), 83:474–478. $^{99m}$Tc is preferred for diagnostic use, and the other radionuclides listed above have therapeutic use.

In one embodiment of the present invention, chelating compounds of the invention comprising acetamidomethyl and/or hemithioacetal sulfur protective groups are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the chelating compounds of the invention.

In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}$TcO$_4^-$ which is in the +7 oxidation level) or sodium perrhenate (i.e., $^{188}$ReO$_4^-$, $^{186}$ReO$_4^-$) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to gluconic acid, glucoheptonic acid, methylene disphosphonate, glyceric acid, glycolic acid, mannitol, oxalic acid, malonic acid, succinic acid, bicine, N,N'-bis(2-hydroxy ethyl) ethylene diamine, citric acid, ascorbic acid and gentisic acid. Good results are obtained using gluconic acid or glucoheptonic acid as the Tc-complexing agent and citric acid for rhenium. When the radionuclide in the form of such an exchange complex is reacted with the chelating compounds of the invention, the radionuclide will transfer to these compounds which bind the radionuclide more strongly to form chelates of the invention. Heating is often required to promote transfer of the radionuclide. Radionuclides in the form of such complexes also are considered to be in "chelatable form" for the purposes of the present invention.

Chelates of $^{212}$Pb, $^{212}$Bi, $^{109}$Pd may be prepared by combining the appropriate salt of the radionuclide with the chelating compound and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation (i.e., in chelatable form). The specific radiolabeling reaction conditions may vary somewhat according to the particular radionuclide and chelating compound involved.

The chelating compound may be radiolabeled to form a radionuclide metal chelate, which then is reacted with a targeting protein, ligand or anti-ligand. Alternatively, the unlabeled chelating compound may be attached to the targeting protein, ligand or anti-ligand and subsequently radiolabeled. Proteins and proteinaceous ligands or anti-ligands (e.g., avidin or streptavidin) as well as non-proteinaceous ligands or anti-ligands (e.g., biotin) contain one or more of a variety of functional groups; e.g., carboxylic acid (COOH) or free amine (—NH$_2$) groups, which are available for reaction with a suitable protein, ligand or anti-ligand conjugation group "Z" on a chelator to bind the chelator to the protein, ligand or anti-ligand. For example, an active ester on the chelator reacts with primary amine groups on lysine residues of proteins to form amide bonds. Alternatively, the protein, ligand or anti-ligand and/or chelator may be derivatized to expose or attach additional reactive functional groups. The derivatization may involve attachment of any of a number of linker molecules such as those available from Pierce Chemical Company, Rockford, Ill. (See the Pierce 1986–87 General Catalog, pages 313–54.) Alternatively, the derivatization may involve chemical treatment of the protein (which may be an antibody), ligand or anti-ligand. Procedures for generation of free sulfhydryl groups on antibodies or antibody fragments are also known. (See U.S. Pat. No. 4,659,839.) Maleimide conjugation groups on a chelator are reactive with the sulfhydryl (thiol) groups.

Alternatively, when the targeting compound is a carbohydrate or glycoprotein, derivatization may involve chemical treatment of the carbohydrate; e.g., glycol cleavage of the sugar moiety of a glycoprotein antibody with periodate to generate free aldehyde groups. The free aldehyde groups on the antibody may be reacted with free amine or hydrazine conjugation groups on the chelator to bind the chelator thereto. (See U.S. Pat. No. 4,671,958.)

Biotin has a terminal carboxy moiety which may be reacted with a suitable ligand conjugation group, such as an amine, hydroxyl in the presence of a coupling agent such as DCC or the like. In addition, the terminal carboxy moiety may be derivatized to form an active ester, which is suitable for reaction with a suitable ligand conjugation group, such as an amine, a hydroxyl, another nucleophile, or the like. Alternatively, the terminal carboxy moiety may be reduced to a hydroxy moiety for reaction with a suitable ligand conjugation group, such as a halide (e.g., iodide, bromide or chloride), toxylate, mesylate, other good leaving groups or the like. The hydroxy moiety may be chemically modified to form an amine moiety, which may be reacted with a suitable ligand conjugation group, such as an active ester or the like.

The radiolabeled targeting proteins, ligands and anti-ligands of the present invention have use in diagnostic and therapeutic procedures, both for in vitro assays and for in vivo medical procedures. One type of therapeutic or diagnostic procedure in which the compounds of the present invention may be employed is a pretargeting protocol. Generally, pretargeting encompasses two protocols, termed the three-step and the two-step. In the three-step protocol, shown schematically below, targeting moiety-ligand is administered and permitted to localize to target.

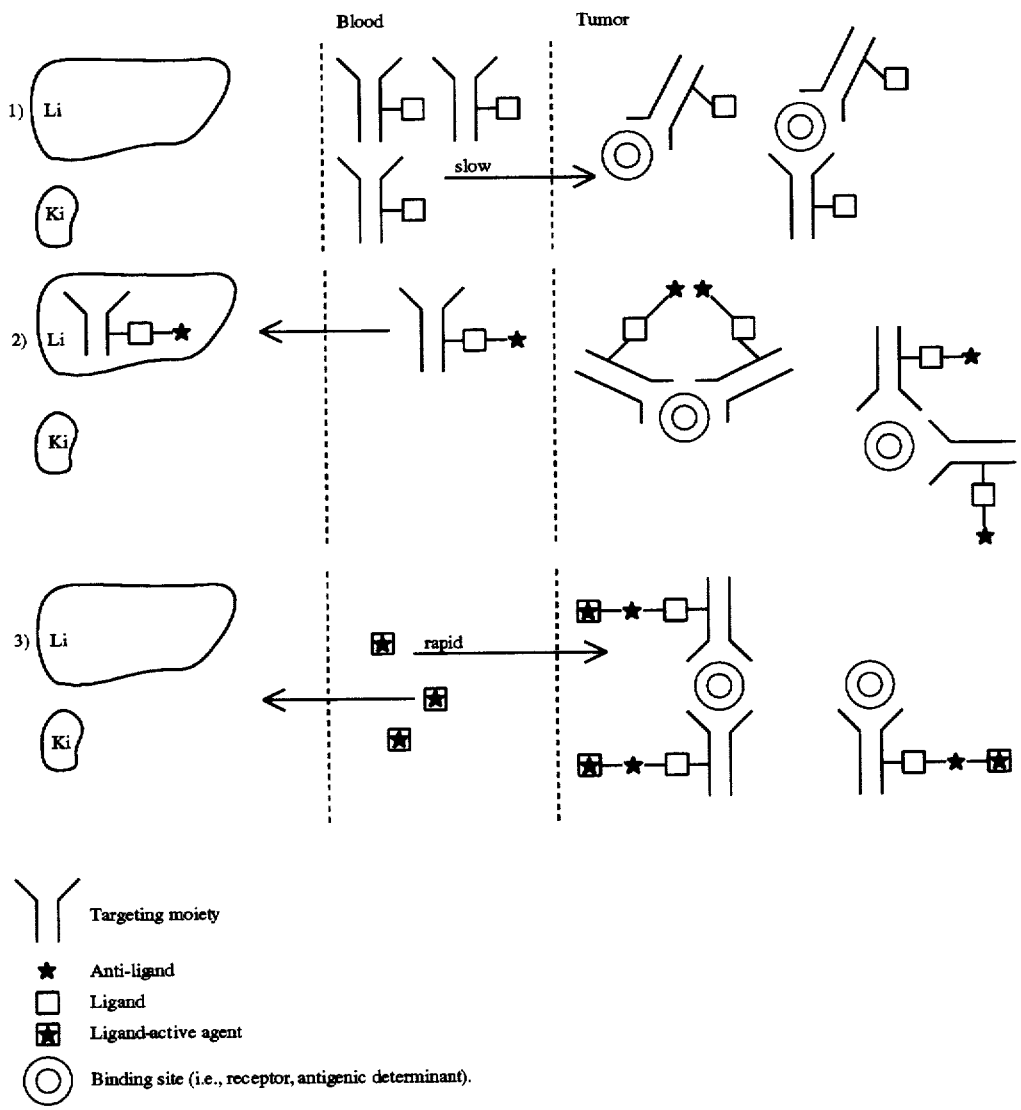

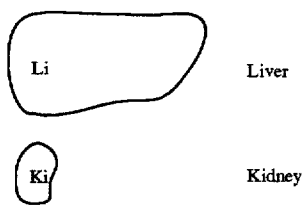

Liver

Kidney

Targeting moiety-ligand conjugates may be prepared in accordance with known techniques therefor. Anti-ligand is then administered to act as a clearing agent and to facilitate and direct the excretion of circulating targeting moiety-ligand. The anti-ligand also binds to target-associated targeting moiety-ligand. Next, a conjugate employing a compound of the present invention is administered, having the following structure:

Ligand————Chelate————Radionuclide

The radiolabeled ligand conjugate either binds to target-associated targeting moiety-ligand-anti-14-gand or is rapidly excreted, with the excretion proceeding primarily through the renal pathway. Consequently, the target-non-target ratio of active agent is improved, and undesirable hepatobiliary excretion and intestinal uptake of the active agent are substantially decreased.

Two-step pretargeting involves administration of targeting moiety-anti-ligand, which may be prepared in accordance with known techniques therefor. After permitting the administered agent to localize to target, a radiolabeled ligand of the present invention is administered. Preferably, as a "step 1.5," a clearing agent is administered to remove circulating targeting moiety-anti-ligand without binding of clearing agent to target-associated targeting moiety-anti-ligand. In this manner, the target-non-target ratio of the radiolabeled ligand is increased, and undesirable hepatobiliary excretion and intestinal uptake of the radiolabeled ligand are substantially decreased.

The radiolabeled proteins, ligands or anti-ligands may be administered intravenously, intraperitoneally, intralymphatically, locally, or by other suitable means, depending on such factors as the type of target site. The amount to be administered will vary according to such factors as the type of radionuclide (e.g., whether it is a diagnostic or therapeutic radionuclide), the route of administration, the type of target site(s), the affinity of the targeting protein for the target site of interest, the affinity of the ligand and anti-ligand for each other and any cross-reactivity of the targeting protein, ligand or anti-ligand with normal tissues. Appropriate dosages may be established by conventional procedures and a physician skilled in the field to which this invention pertains will be able to determine a suitable dosage for a patient. A diagnostically effective dose for a chelate labeled antibody embodiment of the present invention is generally from about 5 to about 35 and typically from about 10 to about 30 mCi per 70 kg body weight. A therapeutically effective dose is generally from about 20 mCi to about 300 mCi. Elevated doses, e.g., ranging from about 2 to about 10 times higher, can be used when pretargeting procedures are employed, because of the decoupling of targeting moiety localization and radionuclide localization. For diagnosis, conventional non-invasive procedures (e.g., gamma cameras) are used to detect the biodistribution of the diagnostic radionuclide, thereby determining the presence or absence of the target sites of interest (e.g., tumors).

The comparatively low intestinal localization of the therapeutic radiolabeled antibodies of the present invention or catabolites thereof permits increased dosages, since intestinal tissues are exposed to less radiation. The clarity and accuracy of diagnostic images also is improved by the reduced localization of radiolabeled antibodies or catabolites thereof in normal tissues. These advantages are also experienced in the practice of the pretargeting aspects of the present invention.

The following examples are presented to illustrate certain embodiments of the present invention.

EXAMPLE I

Synthesis of S-acetamidomethyl-N-t-BOC Isocysteine Trichloroethyl Ester

The synthesis procedure is outlined in FIG. 1. Preparation of S-acetamidomethyl-N-t-BOC isocysteine 6 from 1:

Mercaptosuccinic acid 1 (commercially available) was reacted with cyclopentanone in TosOH to form 2-oxathiolone 2.

To a solution of 2-oxathiolone 2 in benzene (40 mL) and triethylamine (3.28 mL, 23.55 mmol) at 0° C., was added a solution of diphenyl phosphorylazide (5.08 mL, 23.55 mmol) in benzene (5.0 mL). The ice bath was removed and the reaction solution was stirred at room temperature for 1 hour. The solution was washed with water. The water was extracted with benzene. The combined benzene extracts were dried, concentrated to half the original volume, and heated under reflux in an oil bath gradually raised in temperature from 50° C. to 80° C. over 1 hour. The reaction solution was cooled to room temperature, diluted with ethyl acetate (50 mL) and washed twice with a saturated solution of $NaHCO_3$ (30 mL). The organic extracts were dried ($MgSO_4$) and evaporated to give the crude isocyanate 3 as a brown oil (4.92 g).

A suspension of 3 in 6N HCl (45 mL) was heated under reflux for 40 minutes. The reaction solution was cooled, washed twice with ethyl acetate (50 mL). Evaporation of the aqueous extract gave crude isocysteine 4 as an amber oil (4.92 g, theoretical 3.64 g). NMR shows isocysteine plus an aliphatic contaminant.

To half of the crude isocysteine 4 (2.42 g, theoretical 11.61 mmol) in water (3.0 mL) at 0° C. was added N-hydroxyacetamide (1.14 g). To this solution was added dropwise concentrated HCl (0.45 mL). The solution was stored at 0° C. for 3 days. The solution was evaporated to give S-acm isocysteine 5 as a colorless liquid NMR (D2O) 1.95 (s, 3H), 3.35 (dd, 2H), 3.8 (t, 1H), 4.4 (dd, 2H). TLC (c-18, 15% meOH/H2O 1% HOAc, one spot 0.4 Rf.

To a solution of 5 (theoretical 11.61 mmol) in DMF/$H_2O$ 3:2, 25 mL) and triethylamine (3.60 mL, 25–54 mmol) was added di-t-butyl dicarbonate (3.04 g, 13.9 mmol). The reaction was stirred at room temperature for 3 hours and then evaporated. The residue was partitioned between water and ethyl acetate. The water layer was acidified to pH 3.0 with 1.0M HCl and further extracted with ethyl acetate (3×30 mL) and methylene chloride (2×50 mL). The combined organic extracts were dried (MgSO$_4$) and evaporated to give an oil. Purification by chromatography (15% isopropanol/ methylene chloride 2% acetic acid) afforded 6 as an oil which crystallized from acetonitrile. Yield from 2-oxathiolone 2 was 1.90 g (6.21 mmol)=53%.

Conversion of S-acm N-T-BOC isocysteine 6 to S-acm N-T-BOC isocysteine trichloroethyl ester 7:

To an ice cold solution of 6 (1.90 g, 6.21 mmol) and trichloroethanol (0.71 mL, 7.45 mmol) in acetonitrile (12 mL) and methylene chloride (2 mL) was added dicyclohexylcarbodiimide (DCC) (1.47 g, 7.14 mmol) and dimethylamino pyridine (76 mg, 0.62 mmol). The ice bath was allowed to melt and the reaction solution was stirred for 16 hours at room temperature. The reaction was cooled to 0° C., filtered, and evaporated to give an oil which was purified by chromatography (1:1 EtOAc/Hexanes 1% HOAc) to give 7 as an oil (1.25 g, 2.95 mmol) in 47% yield.

EXAMPLE II

Synthesis of N-T-BOC Aminoadipic Acid δt-butyl Ester α-succinimidyl Ester 12

Figure 2:
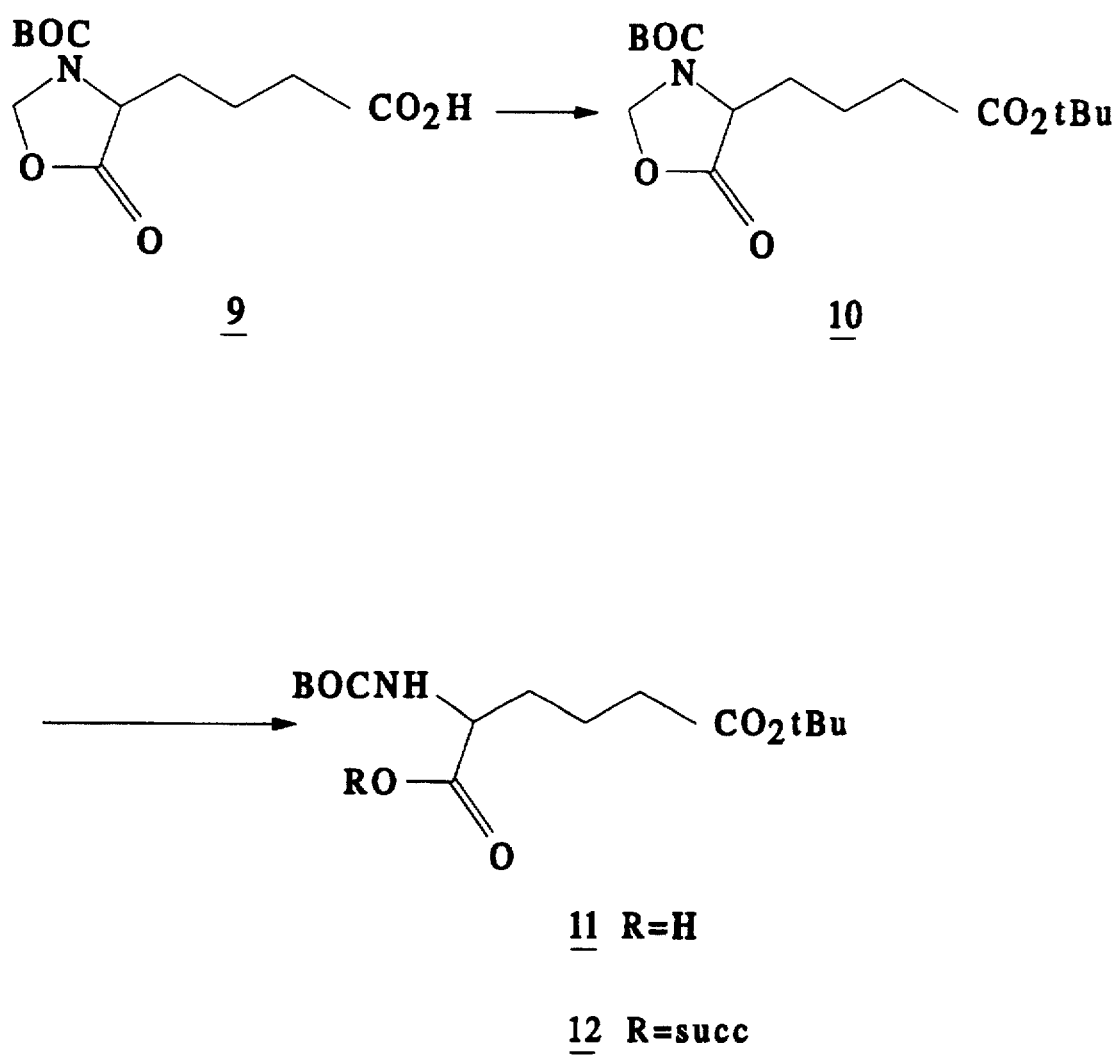

The synthesis procedure is outlined in FIG. 2. Conversion of N-t-BOC oxazolidine aminoadipic acid (9) to N-t-BOC oxazolidine aminoadipic acid t-butyl ester (10):

To an ice cold solution of 9 (3.23 g, 12.4 mmol) in acetonitrile (12 mL) and t-butanol (1.75 mL, 18.6 mmol) were added dimethylaminopyridine (151 mg, 1.24 mmol) and DCC (3.07 g, 14.9 mmol). The reaction was stirred at 0° C. for 69 minutes and then stored at 0° C. for 60 hours. The mixture was filtered. The filtrate was evaporated to give a solid which was chromatographed (25% EtOAc/Hexanes). The t-butyl ester 10 was obtained as a white solid (2.85 g, 8.66 mmol) in 70% yield. Conversion of 10 to N-t-BOC aminoadipic acid δ-t-butyl ester (11):

To a solution of 10 (100 mg, 0.30 mmol) in methanol (2.0 mL) was added 1N NaOH (0.33 mL) dropwise. The solution was stirred for 1 hour and then treated with ethanolamine (0.02 mL, 0.33 mmol). To this solution was added 1N NaOH (0.32 mL, 0.32 mmol). The reaction solution was stirred for 48 hours, concentrated, and then neutralized by the addition of 1N HCl (0.33 mL). The aqueous phase was extracted with EtOAc (25 mL). The aqueous phase was acidified with 1.0N HCl to pH 1 and further extracted with EtOAc (2×50 mL). The combined EtOAc extracts were dried (MgSO$_4$), and evaporated to give an oil. Chromatography (40% EtOAc/ Hexanes 1% HOAc) gave 11 as a colorless oil (60 mg, 0.19 mmol) in 63% yield.

Conversion of 11 to N-t-BOC aminoadipic acid δ-t-butyl ester α-succinimidyl ester 12

To an ice cold solution of 11 (0.97 g, 3.06 mmol) in acetonitrile (6.0 mL) was added N-hydroxysuccinimide (422 mg, 3.67 mmol) and DCC (747 mg, 3.67 mmol). The ice bath was allowed to melt and the reaction solution was stirred at room temperature for 5 hours. The mixture was cooled to 0° C., treated with a few drops acetic acid, and filtered. Evaporation of the filtrate provided 12 as a white solid (1.19 g, 3.06 mmol) in 100% yield.

EXAMPLE III

Synthesis of Succinate Reagent 16

Figure 3:
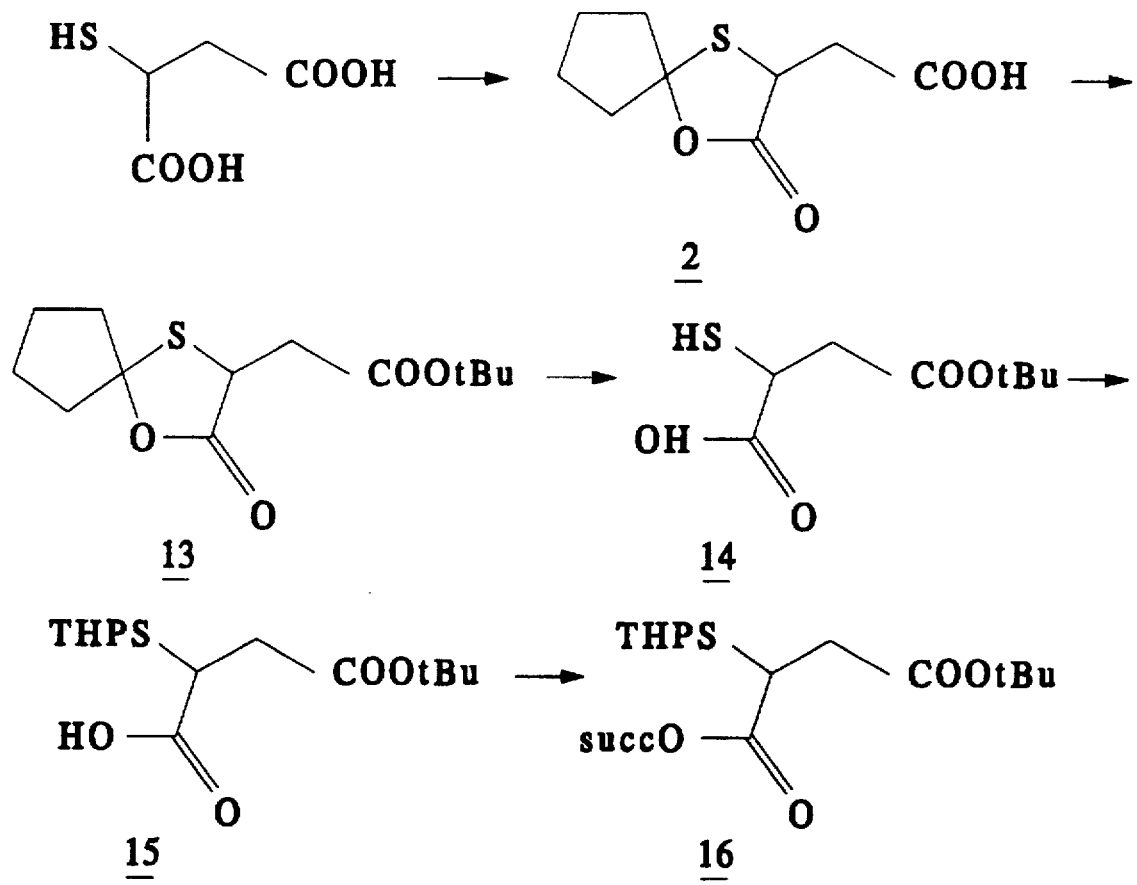
Figure 3:
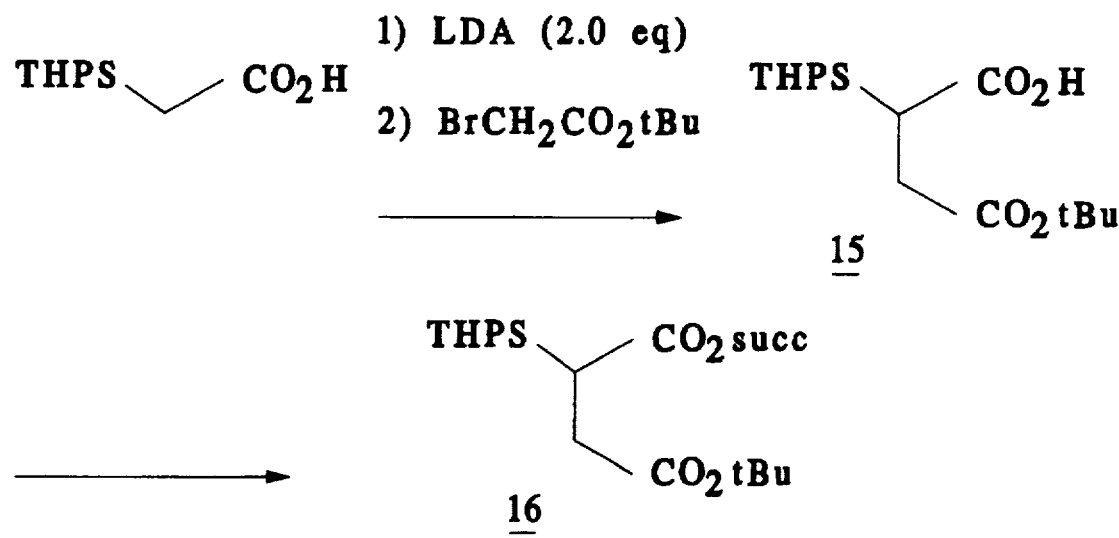

Two procedures for synthesizing compound 16 are outlined in FIG. 3.

Procedure #1: Synthesis of succinate reagent 16 via base opening of oxathiolone:

Conversion of 2 to 2-mercaptosuccinic acid oxathiolone β-t-butyl ester 13

Compound 2 was prepared from 1 as described in Example I.

To an ice cold solution of 2 (1.45 g, 6.30 mmol) in acetonitrile (6.5 mL) and t-butanol (0.89 mL) were added dimethyl aminopyridine (77 mg, 0.63 mmol) and DCC 1.55 g, 7.56 mmol). The reaction was stirred for 1 hour at 0° C. and then stored at 0° C. for 4 days. The product was filtered. The filtrate was evaporated. Chromatography (10% EtOAc/ Hexanes) provided 13 as a yellow oil (1.76 g, 6.15 mmol) in 98% yield.

Conversion of 13 to 2-mercaptosuccinic acid β-t-butyl ester (14)

To a solution of 13 (0.58 g, 1.82 mmol) in acetone (2.0 mL) was added 1N NaOH (1.82 mL, 1.82 mmol). After the reaction solution was stirred for 4 hours, additional 1N NaOH (1.82 mL, 1.82 mmol) was added. The reaction solution was stirred for 20 hours, and then neutralized by the addition of 1.0M HCl (3.6 mL). The aqueous phase was extracted with EtOAc (3×25 mL). The combined EtOAc extracts were washed with brine, dried and evaporated to give an oil. The product was chromatographed (first 10% EtOAc/Hexanes 10% HOAc, 300 mL, then 33% EtOAc/ Hexanes 1% HOAc, 300 mL) to give 14 as colorless oil (0.24 g, 1.16 mmol) in 64% yield.

Conversion of 14 to S-tetrahydropyranylmercaptosuccinic acid β-t-butyl ester (15) and NHS ester 16

To a solution of 14 (240 mg, 1.16 mmol) and tosic acid monohydrate (7 mg, 0.03 mmol) in methylene chloride at −40° C. was added dihydro-2H-pyran (0.11 mL, 1.16 mmol). After the addition, the reaction was warmed to −5° C. and stirred for 30 minutes. The solvent was evaporated. The residue was dissolved in EtOAc (30 mL) and washed with pH 4.0 buffer. The aqueous phase was extracted with EtOAc (2×20 mL). The combined EtOAc extracts were washed with brine, dried and evaporated to give an oil which was used without purification. The oil was dissolved in acetonitrile (2.0 mL), cooled to 0° C., and treated with N-hydroxysuccinimide (160 mg, 1.39 mmol) and DCC (287 mg, 1.39 mmol). The ice bath was allowed to melt and the reaction mixture was stirred at room temperature for 20 hours. The mixture was filtered. The filtrate was evaporated. Chromatography provided 16 as a white solid (145 mg, 0.37 mmol) in 32% yield.

Procedure #2: Synthesis of succinate reagent 16 using LDA

Conversion of S-tetrahydropyranylmercaptoacetic acid (17) to S-tetrahydropyranylmercaptosuccinic acid β-t-butyl ester 15 and NHS ester 16

A solution of lithium diisopropylamide (LDA) was prepared by adding a 1.30M solution of n-butyl lithium in hexanes (13.2 mL, 17.2 mmol) to a solution of diisopropyl amine (2.52 mL, 18.0 mmol) in THF (10.0 mL) at −78° C. The solution was stirred for 20 minutes. To this was added dropwise a solution of S-tetrahydropyranylmercaptoacetic acid (1.32 g, 7.50 mmol) in THF (5.0 mL). The reaction became cloudy. It was stirred at −78° C. for 25 minutes, warmed to 0° C., and stirred for 25 minutes. The reaction was then cooled to −78° C. and treated with a solution of t-butyl bromoacetate (3.2 mL) in THF (2.0 mL). The reaction solution was stirred for 1 hour at −78° C., and for 30 minutes at 0° C. The reaction was quenched by the addition of acetic acid (1.0 mL) in methylene chloride. The mixture was concentrated, diluted with water and ethyl acetate. The aqueous layer was separated, acidified with 1.0M HCl to pH 3.0, and further extracted with EtOAc (2×75 mL). The combined EtOAc extracts were washed with brine, dried, and evaporated to give 15 as a canary yellow oil.

The oil was dissolved in acetonitrile (10.0 mL) and methylene chloride (1.5 mL), cooled to 0° C., and treated with N-hydroxysuccinimide (1.03 g, 9.0 mmol) and DCC (1.86 g, 9.0 mmol). The ice bath was allowed to melt and the reaction mixture was stirred for 4 hours. The mixture was cooled to 0° C. and filtered. The filtrate was evaporated to give an oil which was chromatographed (30% EtOAc/Hexanes) to give 16 as a white foam (1.36 g, 3.51 mmol) in 47% yield.

EXAMPLE IV

Synthesis of Isocys-aminoadipic-mercaptosuccinate Chelating Compound 21

Figure 4:
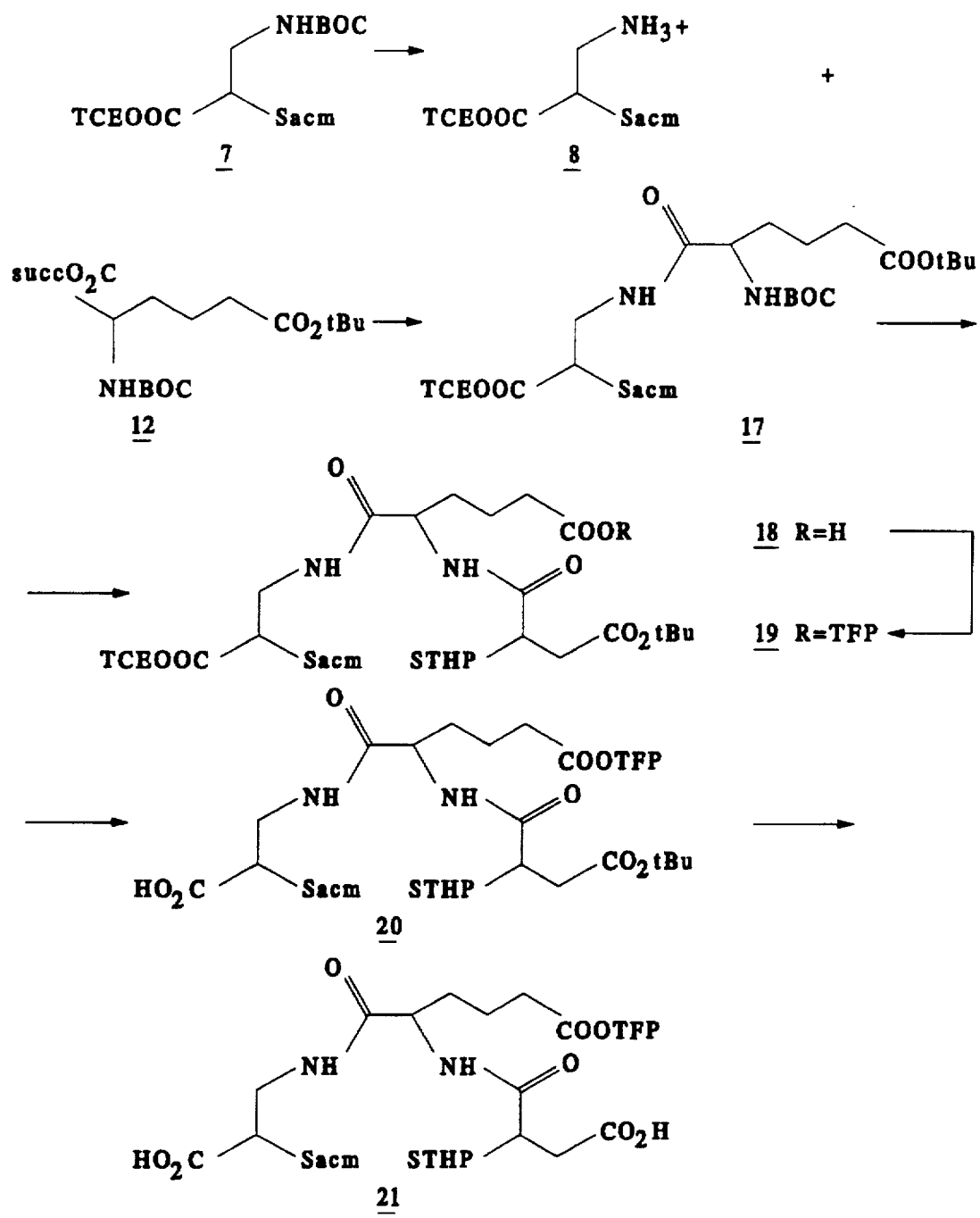

The synthesis procedure is outlined in FIG. 4. Condensation of cysteine 8 with aminoadipic acid derivative 12 to give 17:

To an ice cold solution of S-acm N-T-BOC isocysteine trichloroethyl ester 7, prepared in Example I, (1008 mg, 2.38 mmol) in methylene chloride (7.0 mL) was added trifluoroacetic acid (6.0 mL) dropwise. The solution was stirred at room temperature for 1 hour. The solution was evaporated from carbon tetrachloride (3×50 mL). The residue was dried in vacuo for 18 hours. To an ice cold solution of the residue 8 in DMF (2.5 nil) was added a solution of 12, prepared in Example II, (867 mg, 2.22 mmol) in DMF (3.5 mL). To this was added triethylamine (0.73 mL, 5.24 mmol). The reaction was stirred at room temperature for 6 hours and then evaporated. The residue was partitioned between water and EtOAc. The aqueous phase was extracted with EtOAc (2×50 mL). The combined EtOAc extracts were washed with brine, dried, and evaporated. The product was chromatographed (50% EtOAc/Hexanes 1% HOAc) to give 17 as a white foam (1005 mg, 1.61 mmol) in 68% yield.

Condensation of 17 with succinate reagent 16 to give tripeptide 18

To an ice cold solution 17 (500 mg, 0.81 mmol) in methylene chloride (4.3 mL) was added trifluoroacetic acid (4.3 mL). The ice bath was removed and the reaction was stirred for 1 hour. The solution was evaporated from carbon tetrachloride (3×30 mL). The residue was dissolved in DMF (1.0 mL) and cooled to 0° C. To this was added a solution of 16, prepared in Example III, (376 mg, 0.97 mmol) in DMF (2 mL). Lastly triethylamine was added (0.22 mL, 1.62 mmol). The ice was allowed to melt. The reaction was stirred at room temperature for 21 hours. The solvent was evaporated. The residue was dissolved in EtOAc and washed with pH 4.0 buffer. The aqueous phase was extracted with EtOAc, then acidified with 1.0M HCl to pH 3.0, further extracted with EtOAc (2×30 mL). The combined EtOAc extracts were washed with brine, dried, and evaporated. The residue was chromatographed (99:1 EtOAc:HOAc). The product 18 was obtained as a white solid in 80% yield (480 mg, 0.65 mmol).

Conversion of 18 to TFP ester 19

To an ice cold solution of 18 (480 mg, 0.65 mmol) in acetonitrile (1.5 mL) and methylene chloride (0.5 mL) were added tetrafluorophenol (140 mg, 0.84 mmol) and DCC (161 mg, 0.78 mmol). The ice bath was allowed to melt and the reaction was stirred at room temperature for 20 hours. The reaction was cooled to 0° C., treated with 2 drops acetic acid, and filtered. The filtrate was evaporated. The residue was chromatographed to give 19 as an oil (240 mg, 0.27 mmol) in 42% yield.

Cleavage of TCE ester 19 to give 20

To a solution of 19 (190 mg, 0.21 mmol) in THF (1.4 mL) and 1.0M $KH_2PO_4$ (0.28 mL) was added Zn dust (137 mg, 2.10 mmol). The mixture was stirred for 30 minutes. Additional phosphate buffer (0.28 mL) and Zn dust (137 mg, 2.10 mmol) were added. The reaction was stirred for 80 minutes. Additional phosphate buffer (0.25 mL), THF (1.0 mL), and Zn dust (137 mg, 2.10 mmol) were added. The reaction was filtered. The filtrate was evaporated. The residue was chromatographed to give in the first fractions recovered 19 (60 mg, 0.07 mmol), then in the later fractions 20 as a white foam (40 mg, 0.05 mmol) in 25% yield.

Cleavage of t-butyl ester 20 to give 21

A solution of 20 (40 mg, 0.05 mmol) in formic acid (1.5 mL) was stirred for 5 hours. The solution was evaporated. The product was purified by preparative LC on reverse phase semi-prep C-18 column with 45% $CH_3CN/H_2O$ 1% HOAC as mobile phase. The product 21 was obtained as a film (6 mg, 0.01 mmol) in 16% yield. The compound 21 is a chelating compound of the present invention.

EXAMPLE V

Synthesis of Cysteine Monocarboxylate Chelating Compound 28

Figure 5:
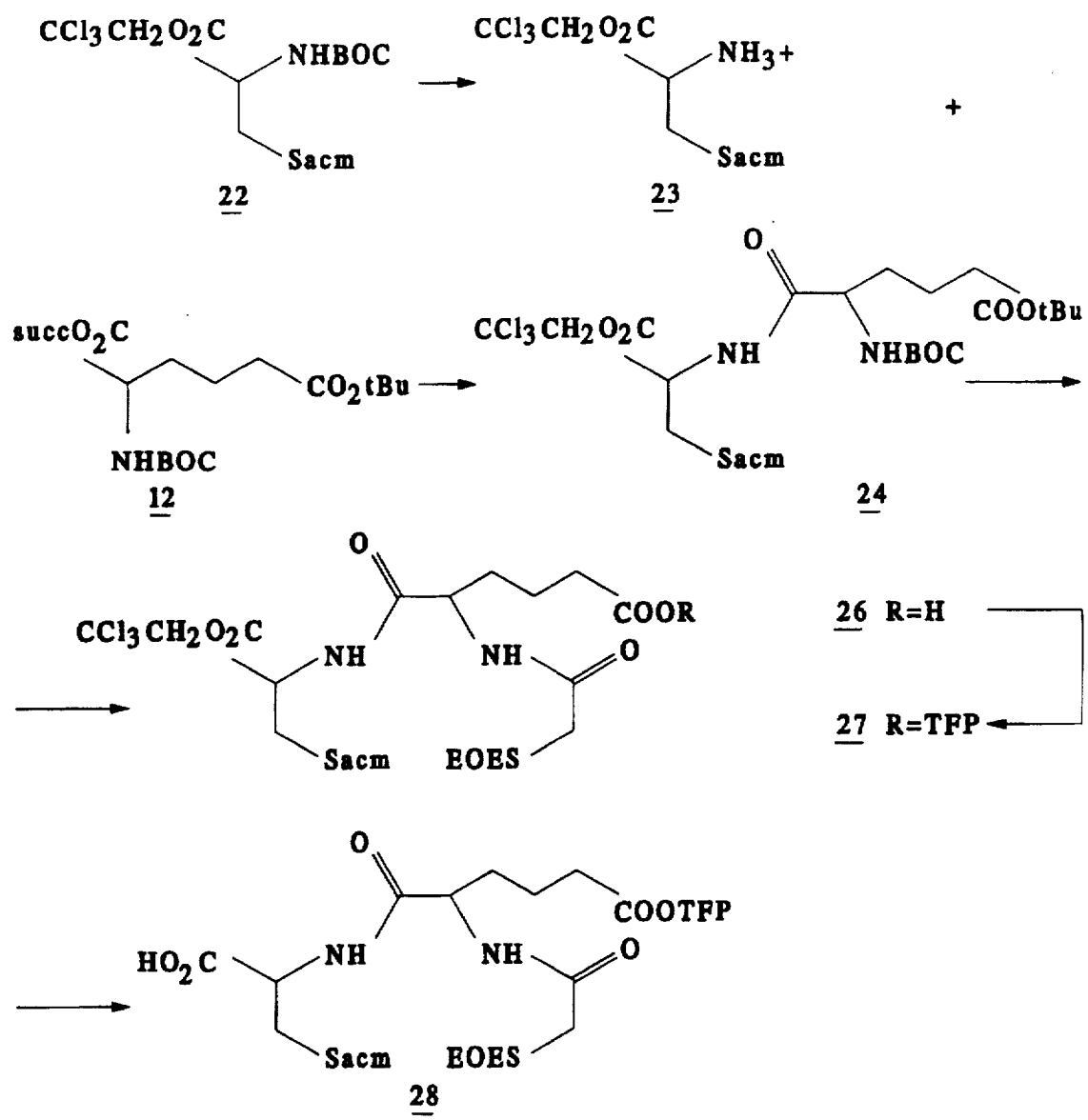

The synthesis procedure is outlined in FIG. 5. t-BOC cleavage and condensation of cysteine 22 with aminoadipic acid derivative 12:

To an ice cold solution of 22 (0.97 g, 2.30 mmol) in methylene chloride (6.0 mL) was added trifluoroacetic acid (6.0 mL). The reaction was stirred at room temperature, then coevaporated with carbon tetrachloride (3×15 mL) and dried in vacuo. The residue (23) was dissolved in dimethyl formamide (1.0 mL) and triethylamine (0.35 mL, 2.53 mmol). To this was added a suspension of N-t-BOC aminoadipic acid-α-NHS-δ-t-butyl ester 12, prepared in Example II, (897 mg, 2.30 mmol) in DMF (2.5 mL). Triethylamine (0.35 mL, 2.53 mmol) was added and the reaction was stirred for 18 hours. The solution was concentrated. The residue was dissolved in EtOAc and washed with pH 4.0 buffer. The aqueous phase was further extracted with EtOAc (2×30 mL). The combined EtOAc extracts were washed with brine, dried, and evaporated to give an oil. Chromatography (75% EtOAc/Hexanes 1% HOAc) gave 24 as a white solid (1.40 g, 2.30 mmol) in 100% yield. FAB MS parent ions 622 and 624.

Deprotection of 24 and condensation with S-ethoxyethyl mercaptoacetic acid NHS ester to give 26

To an ice cold solution of 24 (690 mg, 1.12 mmol) in methylene chloride (6.0 mL) was added trifluoroacetic acid (6.0 mL). The ice bath was removed and the reaction was stirred at room temperature for 2 hours. The solution was coevaporated with carbon tetrachloride (3×10 mL). The residue was dissolved in DMF and triethylamine (0.15 mL, 1.12 mmol). To this solution at 0° C. was added a solution of S-ethoxyethyl mercaptoacetic acid NHS ester (322 mg, 1.23 mmol) in DMF 2.0 mL). Lastly triethylamine (0.31 mL, 2.24 mmol) was added. The ice bath was allowed to melt and the reaction was stirred at room temperature for 18 hours. The solvent was evaporated. The residue was dissolved in EtOAc (30 mL) and washed with pH 4.0 buffer. The aqueous phase was extracted with EtOAc (2×25 mL). The combined EtOAc extracts were dried and evaporated. The residue was chromatographed (50% EtOAc/Hexanes 1% HOAc). The product 26 was obtained as an oil (380 mg, 0.55 mmol) in 50% yield.

Conversion of 26 to TFP ester 27

To a solution of 26 (190 mg, 0.31 mmol) in THF (1.8 mL) was added tetrafluorophenol (65 mg, 0.35 mmol) and DCC (73 mg, 0.35 mmol). The reaction was stirred for 20 hours, cooled to 0° C., and filtered. The filtrate was evaporated. The residue was chromatographed (99:1 EtOAc:HOAc). The product 27 was obtained as colorless oil (150 mg, 0.20 mmol) in 64% yield.

TCE ester cleavage of 27 to give cysteine ligand 28

To a solution of 27 (90 mg, 0.12 mmol) in THF (0–8 mL) and 1.0M $KH_2PO_4$ buffer (0.16 mL) was added Zn dust (78 mg, 1.20 mmol). The suspension was stirred for 40 minutes. Additional phosphate buffer (0.16 mL) and Zn dust (78 mg, 1.20 mmol) were added. The reaction was stirred for 40 minutes, filtered, and rinsed with 50% aqueous acetonitrile (30 mL). The filtrate was evaporated. The residue was chromatographed (15% isopropanol/methylene chloride 2% HOAc). The product 28 was obtained as an oil (60 mg, 0.10 mmol) in 80% yield. Compound 28 is a chelating compound of the present invention.

EXAMPLE VI

Synthesis of Cysteine Succinate Chelating Compound 32

Figure 6:
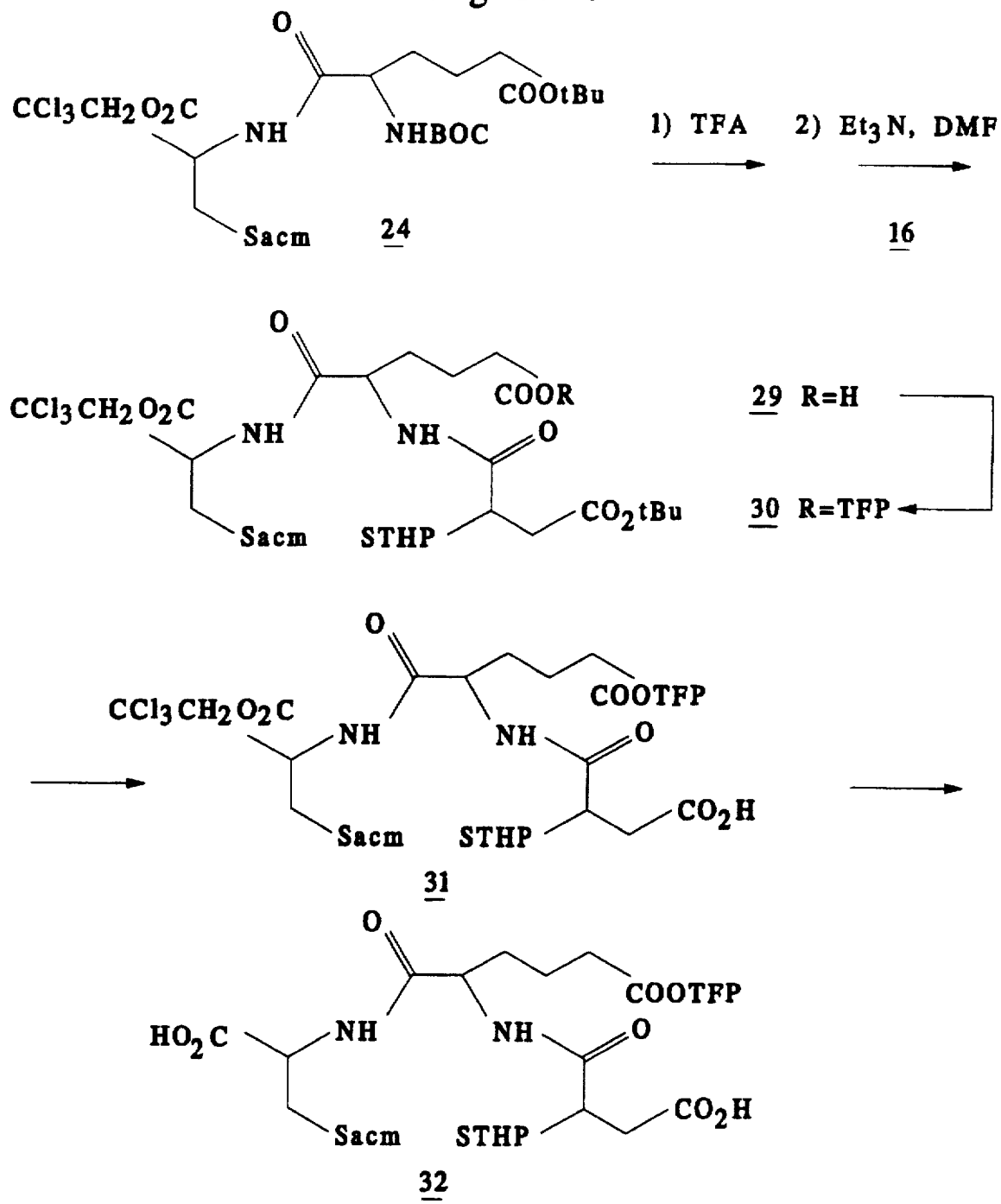

The synthesis procedure is outlined in FIG. 6. t-BOC and t-butyl cleavage of 24 and condensation with succinate reagent 16 to give protected tripeptide 29:

To an ice cold solution of 24, prepared as in Example V, (708 mg, 1.16 mmol) in methylene chloride (6.2 mL) was added trifluoroacetic acid (6.2 mL). The solution was stirred at room temperature for 1.5 hours and then evaporated from carbon tetrachloride (3×15 mL). To the residue dissolved in DMF (2.0 mL) at 0° C. was added a solution of 16, prepared in Example III, (450 mg, 1.16 mmol) in DMF (2.0 mL). The reaction was stirred for 18 hours, and concentrated. The residue was partitioned between EtOAc and pH 4.0 buffer. The aqueous phase was extracted with EtOAc (2×25 mL). The combined EtoAc extracts were washed with brine, dried, and evaporated to give an oil. Chromatography (99:1 EtOAc/HOAc) provided 29 as a white foam (0.39 g, 0.53 mmol) in 46% yield.

Conversion of 29 to TFP ester 30

To an ice cold solution of 29 (390 mg, 0.53 mmol) in acetonitrile (1.0 mL) were added tetrafluorophenol (115 mg, 0.69 mmol) and DCC (131 mg, 0.63 mmol) The reaction was stirred for 18 hours, cooled to 0° C., filtered, and the filtrate was evaporated. Chromatography (75% EtOAc/Hexanes 1%; HOAc) gave 30 as an oil (400 mg, 0.45 mmol) in 85% yield.

Cleavage of t-butyl and trichloroethylester protecting groups to give 32

A solution of 30 (200 mg, 0.22 mmol) in formic acid (7.5 mL) was stirred for 3 hours and then evaporated. The residue was chromatographed (99:1, EtOAclHOAc) to give 31 as a white foam. To a solution of 31 (180 mg, 0.22 mmol) in THF (1.44 mL) were added Zn (144 mg, 2.20 mmol) and 1.0M $KH_2PO_4$ (0.29 mL). The reaction was stirred 40 minutes. Additional Zn (150 mg, 2.29 mmol) and 1.0M $KH_2PO_4$ (0.29 mL) were added. The reaction was stirred for 30 minutes. Additional Zn (150 mg, 2.29 mmol) and 1.0M $KH_2PO_4$ (0.29 mL) were added. The reaction was stirred 20 minutes, filtered, rinsed with acetonitrile (25 mL), 50% aqueous acetonitrile (10 mL), and evaporated to give a solid (140 mg). One third of the crude product was purified by preparative LC on a semi-analytical C-18 reverse LC column with 45% acetonitrile/water 1% acetic acid as the mobile phase. The final chelating compound 32 was obtained as a white film (17 mg, 0.025 mmol). Thus projected yield if all of the crude product had been LC prepped is 34% for the two deprotection steps. Compound 32 is a chelating compound of the present invention.

EXAMPLE VII

Synthesis of DAP-disuccinate 36

Figure 7:
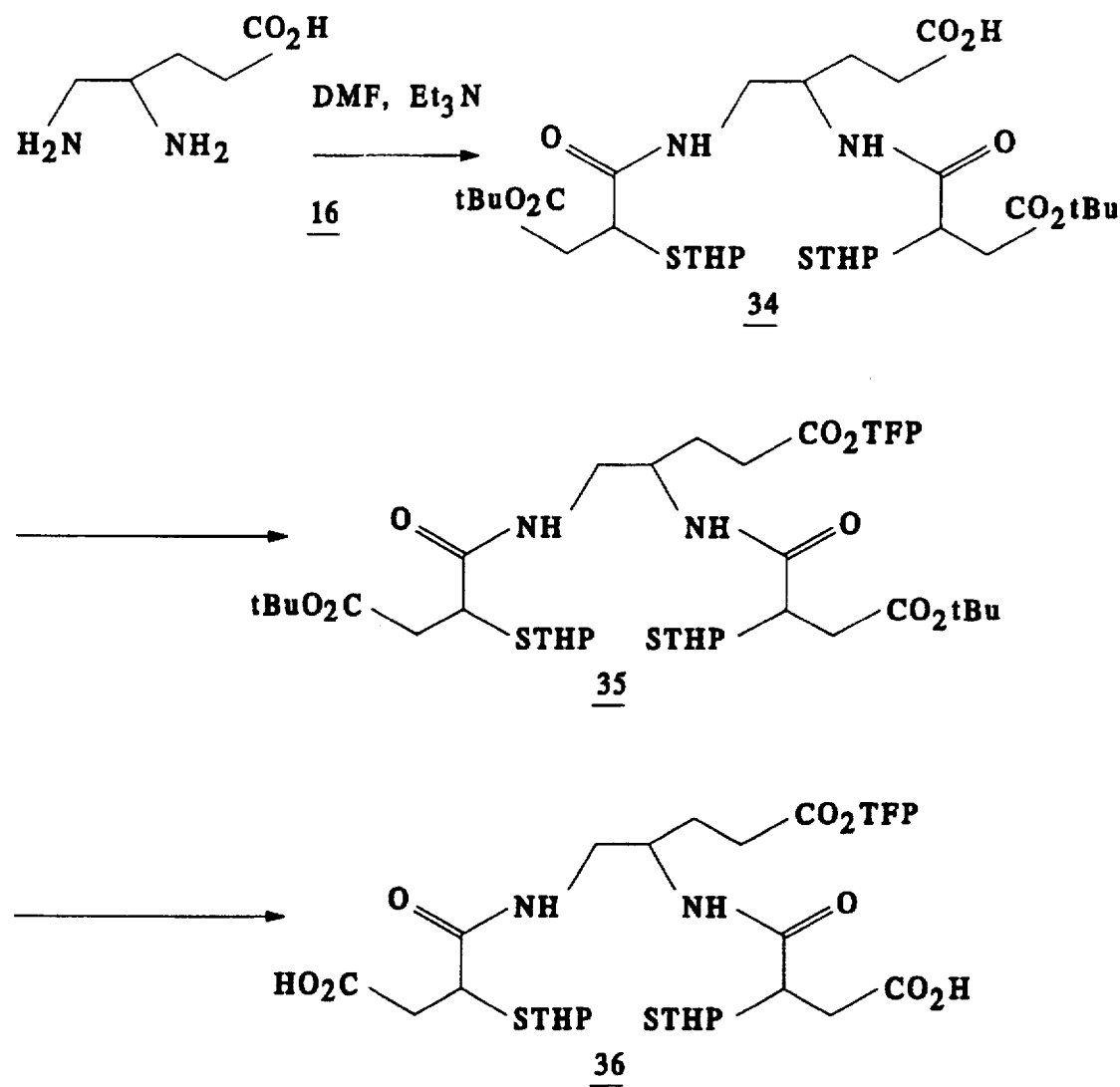

The synthesis procedure is outlined in FIG. 7. Condensation of 4, 5-diaminopentanoic acid (DAP) with succinate reagent 16:

To an ice cold suspension of DAP (338 mg, 1.65 mmol) and 16, prepared in Example III, (1160 mg, 3.0 mmol) in DMF (3.5 mL) was added triethylamine (1.03 mL, 5.77 mmol). The ice bath was allowed to melt and the reaction was stirred at room temperature for 18 hours. The solution was concentrated. The residue was partitioned between EtOAc and pH 4.0 buffer. The aqueous phase was washed with EtOAc (2×50 mL). The combined EtOAc extracts were washed with brine, dried, and evaporated. The residue was chromatographed (50% EtOAc/Hexanes 1% HOAc, 400 mL, then 65% EtOAc/Hexanes 1% HOAc) to give 34 as a white solid (770 mg, 1.13 mmol) in 69% yield.

Conversion of 34 to TFP ester 35

To an ice cold solution of 34 (363 mg, 0.50 mmol) in acetonitrile (1.0 mL) and methylene chloride (0.1 mL) were added tetrafluorophenol (113 mg, 0.68 mmol) and DCC (129 mg, 0.62 mmol). The ice bath was allowed to melt and the reaction was stirred at room temperature for 18 hours. The reaction was cooled to 0° C., treated with 2 drops acetic acid, and filtered. The filtrated was evaporated. The residue was chromatographed (30% EtOAc/Hexanes) to give 35 as a white foam (350 mg, 0.41 mmol) in 80% yield.

Conversion of 35 to discuccinate ligand 36

A solution of 35 (230 mg, 0.27 mmol) was stirred for 2 hours. The solution was coevaporated with toluene and dried in vacuo. Crude 36 was obtained as a white solid (200 mg). Half of the product was purified by preparative LC on a C-18 semi-prep reverse phase column. The first eluting major peak, referred to as "A", was obtained in 22% yield as a white solid (19 mg, 0.03 mmol). The second eluting major peak, referred to as "B" was obtained in 3906 yield (30 mg, 0.05 mmol). High resolution FAB-MS showed parent ions and similar fragmentation patterns for both isomers "A" and "B". Compound 36 (both isomers thereof) is a chelating compound of the present invention.

EXAMPLE VIII

Preparation of Radionuclide Metal Chelates and Attachment of the Chelates to Targeting Proteins 1. 99mTc Chelates: Each of the four chelating compounds synthesized in Examples I–VII (Compounds 21, 28, 32, and 36) was radiolabeled with $^{99m}Tc$ according to the following procedure One mL of sterile water for injection was added to a sterile vial containing a stannous gluconate complex (50 mg sodium gluconate and 1.2 mg stannous chloride dehydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate (0.75 mL, 75–100 mCi, eluted from a "Mo/"Tc generator purchased from DuPont, Mediphysics, Mallinckrodt or E. R. Squibb) was added, and the vial was agitated gently to mix the contents, then incubated at room temperature for 10 minutes to form a $^{99m}$Tc-gluconate complex.

In an alternative procedure for providing the $^{99m}$Tc-gluconate exchange complex, the kit includes a vial containing a lyophilized preparation comprising 5 mg sodium gluconate, 0.12 mg stannous chloride dehydrate, about 0.1 mg gentisic acid as a stabilizer compound, and about 20 mg lactose as a filler compound. The amount of gentisic acid may vary, with the stabilizing effect generally increasing up to about 0.1 mg. Interference with the desired reactions may occur when about 0.2 mg or more gentisic acid is added. The amount of lactose also may vary, with amounts between 20 and 100 mg, for example, being effective in aiding lyophilization. Addition of stabilizer and a filler compound is especially important when the vial contained these relatively small amounts of sodium gluconate and stannous chloride (compared to the alternative embodiment above). One mL of sodium pertechnetate (about 100 mCi) was added directly to the lyophilized preparation. The vial was agitated gently to mix the contents, then incubated as described above to form the $^{99m}$Tc-gluconate complex.

A separate vial containing 0.3 mg of a chelating agent in dry solid form was prepared by dispensing a solution of 0.3 mg chelating agent in acetonitrile into the vial, then removing the solvent under $N_2$ gas. To this vial was then added 0.87 mL of 100% isopropyl alcohol, and the vial was gently shaken for about 2 minutes to completely dissolve the chelating compound. Next, 0.58 mL of this solution of the chelating agent was transferred to a vial containing 0.16 mL of glacial acetic acid/0.2N HCl (2:14), and the vial was gently agitated. Of this acidified solution, 0.5 mL was transferred to the vial containing the $^{99m}$Tc-gluconate complex, prepared above. After gentle agitation to mix, the vial was incubated in a 75° C.±2° C. water bath for 15 minutes, then immediately transferred to a 0° C. ice bath for 2 minutes.

To a separate vial containing 10 mg of the Fab fragment of a monoclonal antibody in 0.5 mL of phosphate-buffered saline, was added 0.37 mL of 1.0M sodium bicarbonate buffer, pH 10.0. The Fab fragment was generated by treating the monoclonal antibody with papain according to conventional techniques. The monoclonal antibody, designated NR-LU-10, recognizes a pancarcinoma antigen. The vial was gently agitated. Other targeting proteins may be substituted for the NR-LU-10 Fab fragment.

The vial containing the acidified solution of the $^{99m}$Tc-labeled chelate (see above) was removed from the ice bath, 0.1 mL of the sodium bicarbonate buffer was added, and the vial was agitated to mix. Immediately, the buffered antibody solution (above) was added, gently agitated to mix and incubated at room temperature for 20 minutes to allow conjugation of the radiolabeled chelate to the antibody.

A column containing an anion exchanger, either DEAE-Sephadex or QAE-Sephadex, was used to purify the conjugate. Thuncolumn was prepared under aseptic conditions as follows. Five 1 mL QAE-Sephadex columns were connected end-to-end to form a single column. Alternatively, a single 5 mL QAE-Sephadex column may he used. The column was washed with 5 mL of 37 mM sodium phosphate buffer, pH 6.8. A 1.2µ filter (available from Millipore) was attached to the column, and a 0.2µ filter was attached to the 1.2µ filter. A 22-gauge sterile, nonpyrogenic needle was attached to the 0.2µ filter.

The reaction mixture was drawn up into a 3 mL or 5 mL syringe, and any air bubbles were removed from the solution. After removal of the needle, the syringe was connected to the QAE-Sephadex column on the end opposite the filters.

The needle cap was removed from the 22-gauge needle attached to the filter end of the column and the needle tip was inserted into a sterile, nonpyrogenic test tube. Slowly, over 2 minutes, the reaction mixture was injected into the column. The eluant collected in the test tube was discarded. The now empty syringe on top of the column was replaced with a 5 mL syringe containing 5 mL of 75 mM (0.45%) sodium chloride solution (from which air bubbles had been removed). The needle at the other end of the column was inserted aseptically into a sterile, nonpyrogenic 10 mL serum vial. Slowly, over 2 minutes, the NaCl solution was injected into the column, and the eluent was collected in the serum vial.

The resulting radiolabeled antibody fragments may be represented as follows:

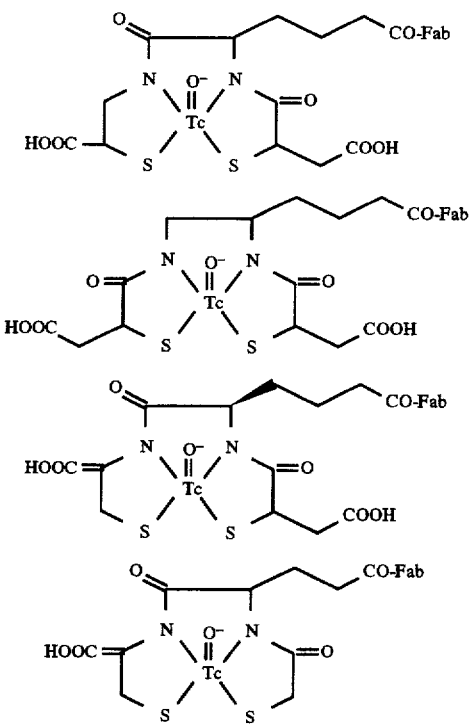

2. $^{188}$Re Chelates

The same chelating compounds may be radiolabeled with $^{188}$Re by a procedure similar to the $^{99m}$Tc labeling procedure. Sodium perrhenate produced from a W-188/Re-188 research scale generator is combined with citric acid (a preferred complexing agent for $^{188}$Re), a reducing agent, and preferably gentisic acid and lactose. The resulting $^{188}$Re-citrate exchange complex is heated with the desired chelating compound, as above. A $C_{18}$ reversed phase low pressure material (Baker $C_{18}$ cartridges) may be used to purify the $^{188}$Re-chelate. A monoclonal antibody or fragment thereof is reacted with the chelate in a buffered solution to bind the chelate thereto, as described for the $^{99m}$Tc procedure. A Sephadex G-25 column may be used to purify the radiolabeled antibody.

EXAMPLE IX

Biodistribution of the four $^{99m}$Tc-labeled antibody fragments prepared in Example VIII was analyzed in a rat model. 100 µg of protein (about 0.5 mCi) was administered intravenously into Sprague-Dawley rats. Each of the four types of radiolabeled antibody fragments (i.e., NR-LU-10 Fab fragments radiolabeled with one of the four different chelating compounds) was injected into three rats. Biodistribution was analyzed at 6 hours post-injection by isolating intestines and kidneys and determining the mCi of injected radioactivity per gram of these tissues, using a dose calibrator. The percentage of injected dose per gram of intestinal and kidney tissue was calculated and averaged to give the mean value for each group of three animals.

The results were compared with data on intestinal localization of radioactivity for radiolabeled antibody fragments of the following formula I (wherein the fragments are labeled with an $N_2S_2$ chelate that lacks carboxylic acid substituents):

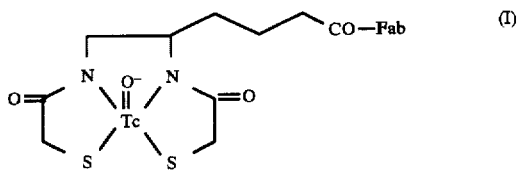

A reduction in intestinal localization of radioactivity was demonstrated for each of the four radiolabeled antibody fragments of the present invention, compared to the radiolabeled fragment of formula (I).

EXAMPLE X

Preparation of Radiolabeled Antibody Fragments

1. $^{99m}Tc$ Chelates: Chelating compounds 21 and 36 (synthesized in Examples IV and VII, respectively) were radiolabeled with $^{99m}Tc$ according to the following procedure (a preferred procedure for these two chelating compounds)

One mL of sterile water for injection was added to a sterile vial containing a stannous gluconate complex (50 mg sodium gluconate and 1.2 mg stannous chloride dehydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate (0.75 mL, 75-100 mCi, eluted from a $^{99}Mo/^{99m}Tc$ generator purchased from DuPont, Mediphysics, Mallinckrodt or E. R. Squibb) was added, and the vial was agitated gently to mix the contents, then incubated at room temperature for 10 minutes to form a $^{99m}Tc$-gluconate complex.

A separate vial containing 0.3 mg of the chelating agent (21 or 36) in dry solid form was prepared by dispensing a solution of 0.3 mg chelating agent in acetonitrile into the vial, then removing the solvent under $N_2$ gas. To this vial was then added 0.87 mL of 100% isopropyl alcohol, and the vial was gently shaken for about 2 minutes to completely dissolve the chelating compound. Next, 0.58 mL of this solution of the chelating agent was transferred to a vial containing 0.16 mL of glacial acetic acid/0.2N HCl (2:14), and the vial was gently agitated. Of this acidified solution, 0.5 mL was transferred to the vial containing the $^{99m}Tc$-gluconate complex, prepared above. After gentle agitation to mix, the vial was incubated in a 75° C.±2° C. water bath for 15 minutes, then immediately transferred to a 0° C. ice bath for 2 minutes.

For compound 36, and whenever the radiolabeling yield for compound 21 was below 40%, the radiolabeled chelate was purified prior to conjugation to an antibody as follows. An SPE-$C_{18}$ extraction column (a reversed phase column available from Baker) was conditioned by washing with 2 mL of ethanol followed by 2 mL of sterile water. The reaction mixture was then loaded onto the top of the column. The column was washed with 2 mL aliquots of 1% ethanol/ 0.01M phosphate (pH=7.0) 6–8 times and dried for 10 minutes under vacuum. The $^{99m}Tc$ chelates were then eluted using 0.5 mL of $CH_3CN$ for compound 21 and 1 mL of $CH_3CN$ for compound 36. The $CH_3CN$ was evaporated under a stream of $N_2$ prior to the conjugation with antibody.

The $^{99m}Tc$ chelates thus purified were attached to the Fab fragment of a monoclonal antibody (designated NR-LU-10) as described in Example VIII. Other targeting proteins may be substituted for the NR-LU-10 antibody fragment.

EXAMPLE XI

Preparation of $^{99m}Tc$ Chelate Using Chelating Compound 32

Compound 32 (prepared in Example VI) was radiolabeled by the following procedure, which is preferred for this particular chelating compound:

One mL of $NaTcO_4$ (~100 mCi) was added to a lyophilized preparation containing 5.0 mg of sodium gluconate, 0.12 mg of stannous chloride dehydrate, 0.1 mg of gentisic acid, and 20 mg of lactose (lyophilization pH=3.5). After incubating the vial at room temperature for 2 minutes, 0.1 mL of compound 32 (1 mg/mL in 90% isopropyl alcohol) was added. Then 0.300 mL of isopropyl alcohol and 0.060 mL of 0.1N HCl were added. 2 cc of air was added into the vial and incubated at 75° C. for 15 minutes. The vial was then immediately transferred to a 0° C. ice bath for 2 minutes.

The resulting $^{99m}Tc$ chelate was attached to an antibody fragment as described in Example VIII. Other targeting proteins may be substituted for the antibody fragment.

EXAMPLE XII

Radiolabeled Ligand Preparation

A. A synthesis scheme for a $N_2S_2$-biotin conjugate is shown below:

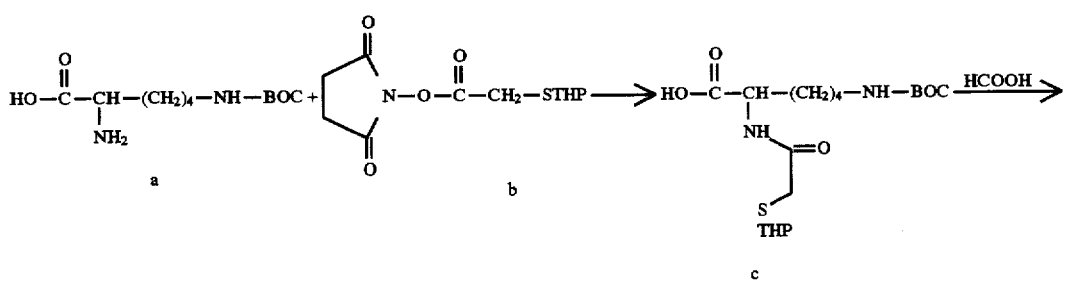

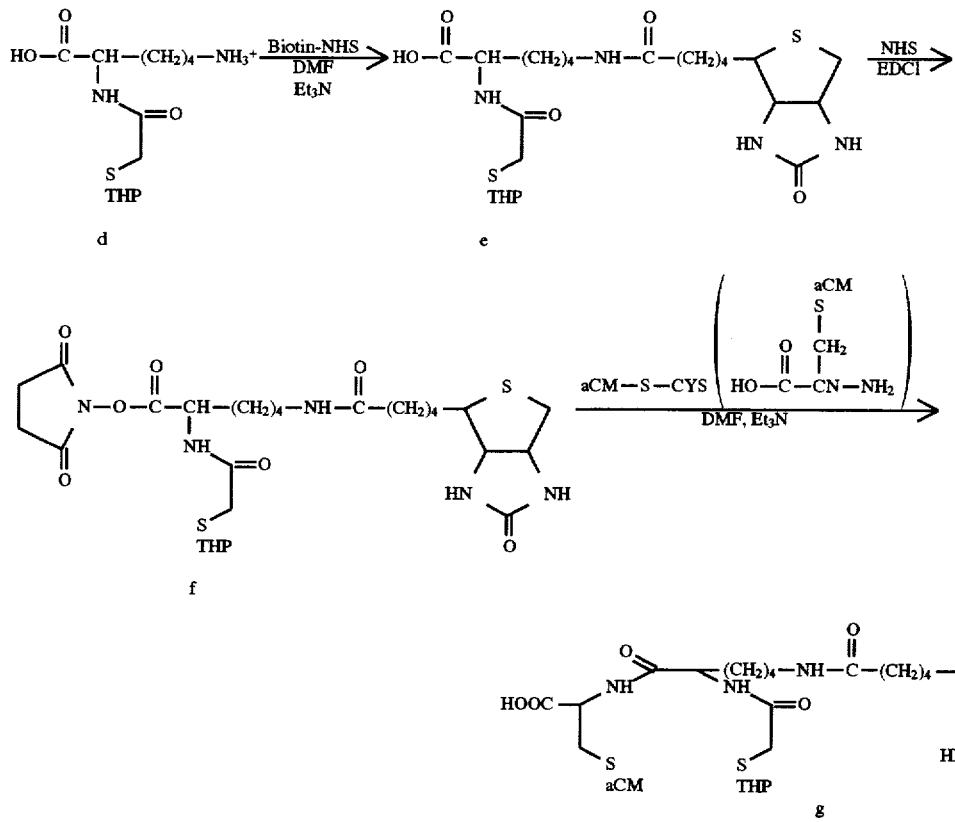

Epsilon-BOC-lysine a (available from Bachem Inc.) is acylated with N-hydroxy succinimidyl-S-tetrahydropyranyl mercaptoacetate b (preparable in accordance with known procedures for protecting thiols as 5-tetrahydropyranyl hemithioacetals, such as Greene et al., *Protective Groups in Organic Synthesis*, 2nd ed., page 291, John Wiley & Sons, Inc., New York, 1990, to give N-alpha-(S-tetrahydropyranylmercapto acetyl)-N-epsilon-BOC-lysine c. The BOC group is cleaved with formic acid, and the resultant amine d is acylated with NHS-biotin to give e. The free carboxyl group of e is activated with NHS and EDCI to give f, which is then coupled to S-acetarnidomethyl-cysteine to give the resultant $N_2S_2$-biotin conjugate g.

B. Diaminopentanoic acid (DAP) core $N_2S_2$-biotin conjugates of the following general formula are contemplated as embodiments of the present invention:

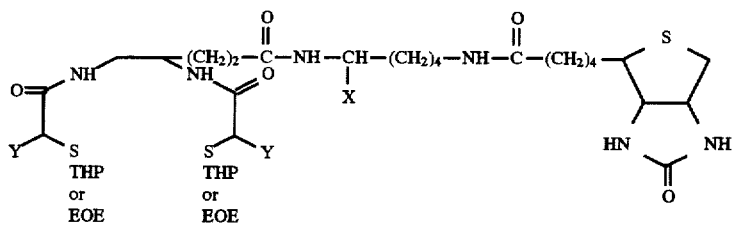

wherein X is H (synthesized using a 5-biotinam4-dopentylamine reactant, wherein the reactant is available from Pierce Chemical Company) or COOH (synthesized using biocytin as a reactant, wherein the reactant is available from Sigma Chemical Company) and wherein Y is H (synthesized using bis-EOE-mercaptoacetyl-DAP as a reactant, wherein the reactant is synthesizable by known procedures) or $CH_2COOH$ (synthesized using bis-THP-mercaptosuccinyl-DAP as a reactant).

A one step synthesis for such DAP core $N_2S_2$-biotin conjugates is shown below:

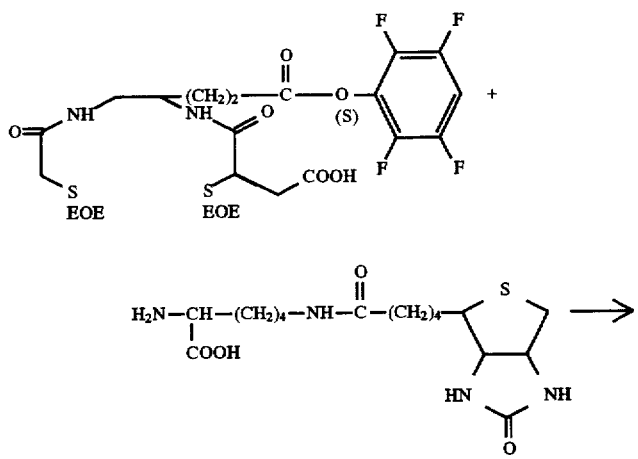

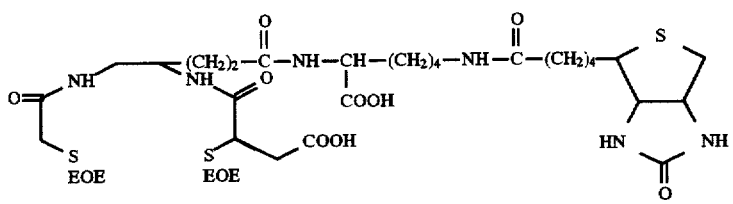

A suspension of $N_2S_2$-tetrafluorophenylester or thioester a and biocytin b is heated at 100° C. for 10 minutes. The product is purified by C-18 flash chromatography to afford the $N_2S_2$-biotin amide product. The 5-biotinamidopentylamine and $N_2S_2$-tetrafluorophenyl ester reaction occurs analogously.

C. In the preparation of a conjugate as shown below, the following procedure may be employed.

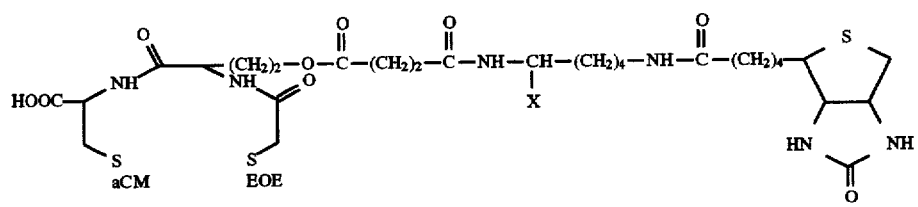

1. A serine succinate reagent as shown below was produced as follows:

(a) t-butyl, N-hydroxy-succinimidyl succinate (LG694-73): To an ice cold solution of succinic acid mono-t-butyl ester (870 mg, 5.0 mmol) and NHS (630 mg, 5.5 mmol) in acetonitrile (7.0 mL) was added DCC (1130 mg, 5.5 mmol). The reaction was allowed to warm to room temperature and stirred for 4.5 hours. The reaction was cooled to 0° C., treated with 0.1 mL acetic acid, and filtered. The filtrate was evaporated to give a gummy solid (1280 mg, theoretical yield). $^1$H NMR (CDCl$_3$): 1.40 (s, 9H), 2.60 (t, 2H), 2.80 (s, 4H), 2.90 (t, 2H).

(b) serinyl succinate (LG694-97): To an ice cold suspension of sodium hydride (60 mg, 2.49 mmol) in DMF (1.0 mL), was added a solution of N-BOC serine (170 mg, 0.83 mmol). The suspension was stirred for 30 minutes and then treated with a solution of t-butyl, N-hydroxy-succinimidyl succinate (225 mg, 0.83 mmol) in DMF (1.0 mL). The suspension was warmed to room temperature and stirred for 16 hours. The reaction was quenched at 0° C. by the addition of a solution of acetic acid (0.1 mL) in EtOAc (1.0 mL). The suspension was partitioned between EtOAc and pH 4.0 buffer. The aqueous was extracted with EtOAc (2×30 mL). The aqueous was acidified to pH 1.0 with 1.0M HCl and further extracted with EtOAc (30 mL). The combined EtOAc extracts were washed with brine, dried, and evaporated to give an oil. Chromatography afforded the product as a colorless oil (190 mg, 0.53 mmol, 53%). $^1$H NMR (CDCl$_3$): 1.40 (2 overlapping singlets, 18H), 2.55 (broad s, 4H), 4.40–5.50 (m, 2H), 4.60 (broad s, 1H) 5.50 (broad d, 1H). MS m/e (rel intensity): 362 (M+H, 13), 337 (22), 250 (52), 154 (100).

(c) serinyl succinate NHS ester (LG694-79): To an ice cold solution of serinyl succinate (600 mg, 1.66 mmol) and NF-S (229 mg, 1.99 mmol) in acetonitrile (2.5 mL) was added DCC (394 mg, 1.91 mmol). The reaction was warmed to room temperature and stirred for 2 hours. The reaction was cooled to 0° C., treated with acetic acid (0.1 mL), and filtered. The filtrate was evaporated to give the product as an oil (760 mg, 1.66 mmol, theoretical yield). $^1$H NMR (CDCl$_3$): 1.45 (2 overlapping singlets, 18H), 2.55–2.70 (m, 4H), 2.85 (s, 4H), 4.55 (dd, 2H), 5.05 (broad s, 1H), 5.60 (broad d, 1H).

2. A cysteine-serine succinate reagent as shown below was produced as follows:

(a) S-acm-N-tBOC cysteine TCE ester (JRW 443-14): DCC (794 mg, 3.85 mmol) was added to a solution of S-acm-N-tDOC cysteine (966 mg, 3.50 mmol) and N,N-dimethyl aminopyridine (47 mg, 0.385 mmol) in trichloroethanol (0.37 mL, 3.85 mmol) and acetonitrile (18 mL). The suspension was stirred at room temperature for 48 hours. The suspension was filtered. The filtrate was evaporated. The residue was dissolved in EtOAc (75 mL) and washed with saturated NaHCO$_3$ (2×50 mL). The EtOAc was dried, evaporated to give an oil which was crystallized from ether/hexanes to give the product as a white solid (500 mg, 1.22 mmol, 3506) $^1$H NMR (CDCl$_3$): 1.50 (s, 9H), 2.05 (s, 3H), 3.10 (dd, 2H), 4.40–4.60 (m, 2H), 4.60–4.95 (overlapping dd and s, 3H), 5.70 (broad d, 1H), 6.90 (broad s, 1H). M.P. 76°–77° C.

(b) cys-ser-succinate (LG 694-80): To an ice cold solution of S-acm-N-tBOC cysteine TCE ester (772 mg, 1.66 mmol) in CH$_2$Cl$_2$ (3.0 mL), was added trifluoroacetic acid (4.0 mL). The reaction was warmed to room temperature and stirred for 1 hour. The solution was coevaporated with carbon tetrachloride (3×30 mL). The residue was dissolved in DMF (1.5 mL), cooled to 0°, and treated with triethylamine (0.24 mL, 1.72 mmol). To this solution was added a solution of serinyl succinate NHS ester (760 mg, 1.66 mmol) in DMF (1.5 mL). To this was added triethylamine 0.48 mL, 3.32 mmol). The reaction was warmed to room temperature and stirred for 16 hours. The solution was diluted with EtOAc (50 mL) and washed with 0.1M HCl, brine, dried, and evaporated to give an oil (1.4 g). The oil was chromatographed (50% EtOAc:Hexanes 1% HOAc, 700 mL, then 75% EtCAc:Hexanes 1% HOAc, then 99:1 EtOAc:HOAc, 200 mL) to give the product as an oil (200 mg, 0.30 mmol, 18%). $^1$H NMR (CDCl$_3$): 1.50 (overlapping singlets, 18H), 2.05 (s, 3H), 2.55 (broad s, 4H), 3.15 (dd, 2H), 4.40–4.65 (m, 5H), 4.70–5.05 (overlapping broad s, dd 3H), 5.70 (broad d, 1H), 6.85 (broad s, 1H), 7.75 (broad d, 1H). MS m/e (rel intensity): 668 (M+2, 5), 666 (M, 5), 568 (11), 510 (19), 439 (25), 57 (100).

Alternatively and preferably, cys-ser-succinate is prepared as set forth below.

(b') N-t-BOC-(O-t-butyldimethylsilyl) serine (LG762-21): To a solution of N-BOC-serine (615 mg, 3.00 mmol) and imidazole (449 mg, 6.60 mmol) in DMF (10.0 mL), was added t-butyldimethylsilyl chloride (994 mg, 6.60 mmol). The reaction solution was stirred at room temperature for 15 hours and then concentrated. The residue was dissolved in EtOAc (50 mL) and washed with water (25 mL), brine (25 mL), and dried to give the product as a white foam (1.00 g, 3.0 mmol, theoretical yield). $^1$H NMR (DMSO): 0.05 (s, 4H), 0.90 (s, 9H), 1.40 (s, 9H), 3.80 (t, 2H), 4.10 (m, 1H), 6.75 (m, 1H).

N-t-BOC-serine-(O-t-butyldimethylsilyl)-N-hydioxy succinimidate (LG762-22): To an ice cold solution of N-t-BOC-serine-O-t-butyldimethylsilyl ether (1.03 g, 3.0 mmol) in acetonitrile (4.5 mL) was added NHS (414 mg, 3.60 mmol) followed by DCC (712 mg, 3.45 mmol). The solution was warmed to room temperature and stirred for 16 hours. The mixture was treated with acetic acid (0.10 mL), cooled to 0°, and filtered. The filtrate was evaporated to give the product as a white foam (1.25 g, 3.0 mmol, theoretical yield). $^1$H NMR (DMSO): 0.05 (s, 4H), 0.90 (s, 9H), 1.40 (s, 9H), 3.830 (s, 4H), 3.90 (m, 2H), 4.50 (m, 1H), 7.45 (d, 1H).

[(S-acetamido-methyl)-(trichloroethyl)]-cysteinyl.-N-BOC-(O-t-butyldimethylsilyl)-serine (LG762-32): To a solution of S-acm-N-tBOC cysteine TCE ester (1.02 g, 2.41 mmol) in CH$_2$Cl$_2$ (5.6 mL) was added trifluoroacetic acid (5.6 mL). The solution was stirred at room temperature for 1 hour and then coevaporated with CCl$_4$ (3×30 mL). The residue was dissolved in DMF. To this solution at 0° was added a solution of N-t-BOC-serine-O-t-butyldimethylsilyl-succinimidyl ester (1.00 g, 2.41 mmol) in DMF (5.0 mL). To this was added triethylamine (0.84 mL, 6.02 mmol). The reaction solution was stirred at room temperature for 16 hours. Additional triethylamine (0.20 mL) was added and the reaction was stirred for 1 hour. The, solution was concentrated. The residue was dissolved in EtOAc (40 mL) and washed with pH 4.0 buffer. The aqueous was washed with EtOAc (30 mL). The combined EtOAc extracts were washed with brine, dried, and evaporated to give an oil. The oil was chromatographed (1:1 EtOAc:Hexanes 1% HOAC) to give the product as a white foam (0.89 g, 1.52 mmol, 63%). $^1$H NMR (DMSO): 0.05 (s, 5H), 0.80 (s, 9H), 1.35 (s, 9H), 1.85 (s, 3H), 2.95 (ddd, 2H), 3.70 (m, 2H), 4.20 (m, 3H), 4.60 (m, 1H), 4.85 (dd, 2H), 6.65 (broad d, 1H), 8.55 (m, 2H).

(S-acetamidomethyl)-trichloroethyl-cysteinyl-N-BOC-serine (LG7G2-28): A solution of [(S-acetamidomethyl)-(trichloroethyl)]-cysteinyl-N-BOC-(O-t-butyldimethylsilyl) -serine (200 mg, 0.34 mmol) in 3:1:1 HOAc:H$_2$O:THF (1.3 mL) was stirred at room temperature for 60 hours. The solution was partitioned between EtOAc and water. The aqueous was extracted with EtOAc (2×20 mL). The combined EtOAc extracts were washed with brine, dried, and evaporated to give the product as an oil (175 mg, 0.34 mmol, theoretical yield). $^1$H NMR (CDCl$_3$): 1.40 (s, 9H), 1.95 (s, 3H), 3.05 (ddd, 2H), 3.65 (dd, 1H), 4.05 (dd, 1H), 4.15–4.50 (m, 3H), 4.70 (dd, 2H), 4.90 (m, 1H), 5.75 (m, 1H), 6.70 (m, 1H), 7.75 (m, 1H).

[(S-acetamidomethyl)-(trichloroethyl)]cysteinyl-N-BOC-[O-(mono-t-btyl)-succinate]-serine (LG G94-80): To an ice cold solution of (S-acetamidomethyl)-trichloroethyl-cysteinyl-N-BOC-serine (90 mg, 0.18 mmol), succinic acid mono-t-butyl ester (31 mg, 0.18 mmol), and DMAP (24 mg, 0.19 mmol) in THF (0.6 mL), was added DCC (43 mg, 0.21 mmol). The solution was warmed to room temperature and stirred for 18 hours. The mixture was filtered and rinsed with cold acetonitrile. The filtrate was evaporated. The residue was chromatographed (50% EtOAc:Hexanes 1% HOAc, 300 mL, then 75% EtOAc:Hexanes 1% HOAc, 300 mL) to give the product as an oil (60 mg, 0.09 mmol, 51%). $^1$H NMR (CDCl$_3$): 1.50 (s, 18H), 2.05 (s, 3H), 2.60 (broad s, 4H), 3.10 (m, 2H), 4.35–4.60 (m, 5H), 4.60–5.05 (overlapping dd and s, 3H), 5.70 (m, 1H), 6.75 (broad s, 1H), 7.70 (broad d, 1H).

(c) [(S-acetamidomethyl)-(trichloroethyl)]cyisteinyl-N-[(S-2-ethoxyethyl)mercaptoacetyl]-[O-succinyl]-serine (LG64)4-81): To an ice cold solution of cys-ser-succinate (200 mg, 0.30 mmol) in CH$_2$Cl$_2$ (2.0 mL), was added trifluoroacetic acid (2.0 mL). The solution was stirred at room temperature for 1 hour. The solution was coevaporated with carbon tetrachloride (3×30 mL). The residue was dissolved in DMF (0.4 μmL) and cooled to 0°. To this solution was added triethylamine (42 µL, 0.30 mmol). To this was added S-ethoxyethyl mercaptoacetic acid succinimidyl ester (94 mg, 0.36 mmol) and triethylamine (84 µL, 0.60 mmol). The ice bath was allowed to melt and the reaction was stirred at room temperature for 18 hours. The solution was diluted with EtOAc (50 mL) and washed with pH 4.0 buffer. The aqueous was extracted with EtOAc (25 mL). The combined EtOAc extracts were washed with brine, dried, and evaporated to give an oil. The oil was chromatographed (23 mm column, 1:1 EtOAc:Hexanes 1% HOAc, 400 mL, then 99:1 EtOAc:HOAc, 700 mL, and lastly 10% IPA:EtOAc 1% HOAc) to give the product as a foam (80 mg, 0.12 mmol, 41%). $^1$H NMR: 1.25 (t, 3H), 1.50 (d, 3H), 2.05 (s, 3H), 2.50–2.70 (m, 4H), 3.30 (m, 2H), 3.40–4.30 (m, 8H), 4.35–4.95 (m, 8H), 6.90 (broad s, 1H), 7.55–7.65 (broad t, 1H), 7.90–8.05 (broad t, 1H). MS m/e: 678 (M+Na), 610, 391, 149.

(d) [(S-acetamidomethyl)-(trichloroethyl)]cysteinyl-N-[(S-2-ethoxyethyl)mercaptoacetyl]-[O-(tetrafluorophenyl) succinate)serine (LG694-82): To an ice cold solution of cysteine-ser-succ SEOE ma (55 mg, 0.08 mmol) in THF (0.50 mL), were added tetrafluorophenol (18 mg, 0.11 mmol) and DCC (19 mg, 0.10 mmol). The ice bath was removed and the solution was stirred at room temperature for 18 hours. The mixture was cooled to 0°, treated with acetic acid (0.1 mL), and filtered. The filtrate was evaporated to give an oil. The oil was chromatographed (1:1 EtOAc:Hexanes 1%, HOAc, 200 mL, then 99:1 EtOAc:HOAc, 200 mL) to give the product as an oil (45 mg, 0.055 mmol, 70%). $^1$H NMR (CDCl$_3$): 1.20–1.35 (m, 3H), 1.55 (d, 3H), 2.10 (s, 3H), 2.82 (t, 2H), 3.05–3.15 (m, 4H), 3.40 (m, 2H), 3.50–3.85 (m, 2H), 4.35–5.05 (m, 9H), 6.70 (broad s, 1H), 6.90–7.15 (m, 1H), 6.90–7.15 (m, 1H), 7.70 (m, 1H), 8.20 (broad s, 1H). MS m/e (rel intensity): 806 (M+2, 14), 804 (M, 12), 761 (64), 759 (52), 735 (35), 733 (28), 689 (37), 687 (37), 663 (410 (50), 155 (100).

(e) [S-acetamidomethyl)cysteinyl-N-[(S-2-ethoxy)mercaptoacetyl]-[O-(tetrafluorophenyl)succinate-serine (LG694-685): To a solution of the TFP ester (30 mg, 0.037 mmol) in THF (0.4 mL) and 1.0M KH$_2$PO$_4$ (80 µL) was added zinc dust (39 mg, 0.59 mmol). After 1 hour, additional 1.0M KH$_2$PO$_4$ (80 µL) and zinc dust (39 mg, 0.59 mmol) were added. The mixture was agitated in a sonicator for 2 hours. The mixture was filtered, rinsed with acetonitrile and 50% CH$_3$CN/H$_2$O 1% HOAc. The filtrate was evaporated. The residue was chromatographed (10% IPA:CH$_2$Cl$_2$ 1% HOAc, 50 mL, then 25% IPA:CH$_2$Cl$_2$ 2% HOAc) to give the product as a foam (14 mg, 0.02 mmol, 57%). $^1$H NMR (CDCl$_3$): 1.25 (t, 3H), 1.60 (d, 3H), 2.05 (s, 3H), 2.85 (t, 2H), 3.10 (m, 4H), 3.35 (m, 2H), 3.40–3.80 (m, 2H), 4.30–5.00 (m, 9H), 6.65 (m, 1H), 6.90–7.10 (m, 1H), 7.70 (m, 1H), 8.20 (broad s, 1H).

3. The cysteine-serine succinate reagent is then utilized as shown below to form the conjugate product.

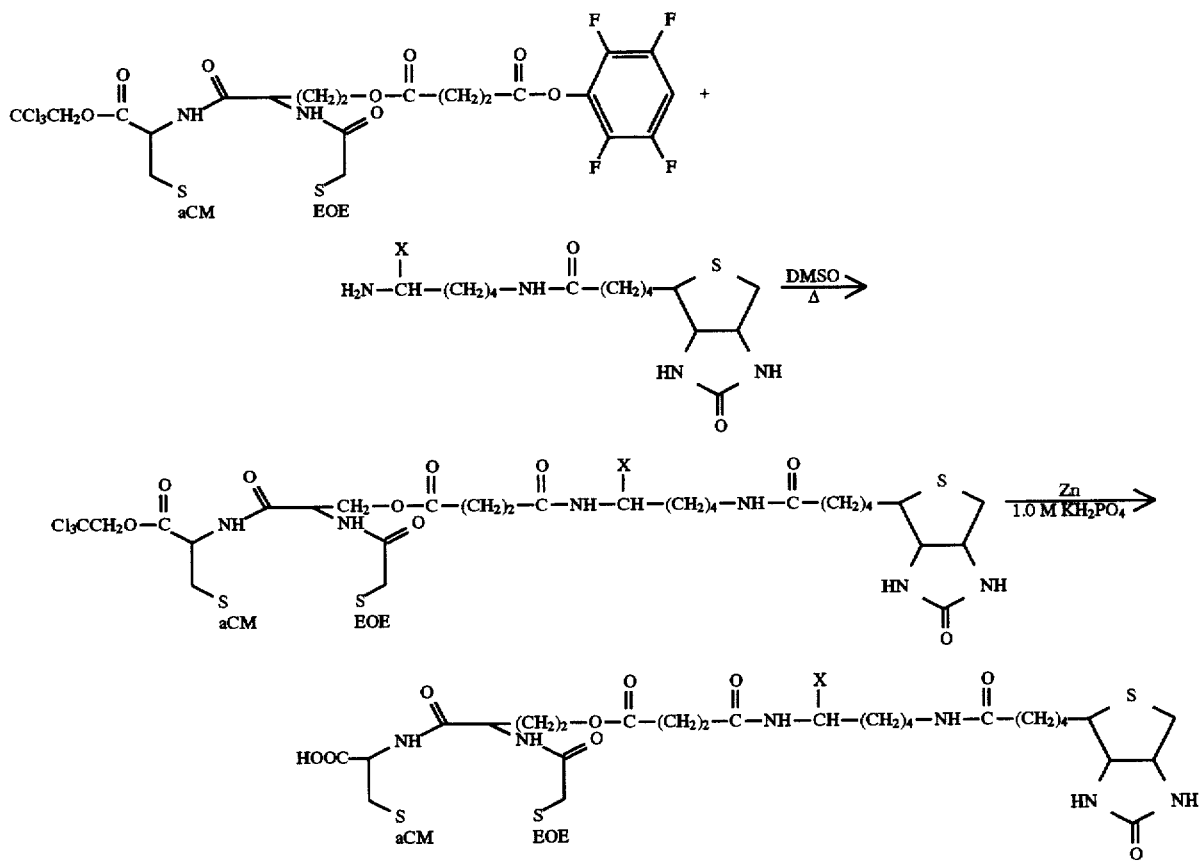

A suspension of biocytin (X amidopentylamine (X=H) and the cysteine-serine succinate reagent in DMSO is heated for 10 minutes. The product is purified by C-18 chromatography. The trichloroethyl ester protecting group is cleaved with zinc dust in 1.0M potassium-dihydrogen phosphate to afford the final product.

EXAMPLE XIII

Preparation of Targeting Moiety-Ligand and Targeting Moiety-Anti-Ligand Conjugates A. Preparation and Characterization of Biotinylated Antibody Biotinylated NR-LU-10 was prepared according to either of the following procedures. The first procedure involved derivitization of antibody via lysine ε-amino groups. NR-LU-10 was radioiodinated at tyrosines using chloramine T and either $^{125}$I or $^{131}$I sodium iodide. The radioiodinated antibody (5–10 mg/ml) was then biotinylated using biotinamido caproate NHS ester in carbonate buffer, pH 8.5, containing 5% DMSO, according to the scheme below.

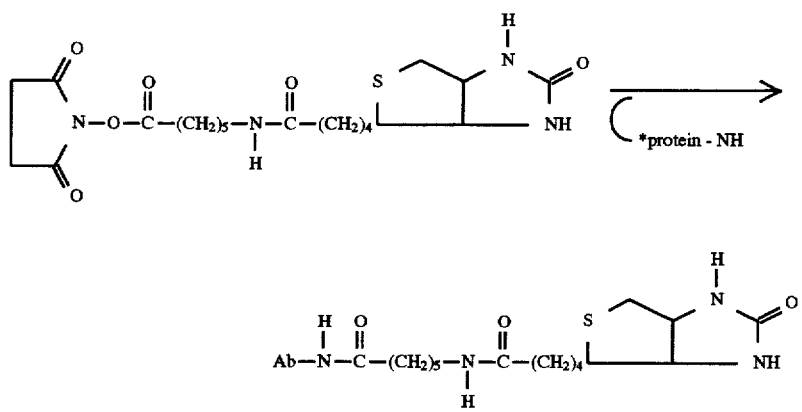

The impact of lysine biotinylation on antibody immunoreactivity was examined. As the molar offering of biotin:antibody increased from 5:1 to 40:1, biotin incorporation increased as expected (measured using the HABA assay and pronase-digested product) (Table 1, below). Percent of biotinylated antibody immunoreactivity as compared to native antibody was assessed in a limiting antigen ELISA assay. The immunoreactivity percentagre dropped below 70% at a measured derivitization of 11.1:1; however, at this level of derivitization, no decrease was observed in antigen-positive cell binding (performed with LS-180 tumor cells at antigen excess). Subsequent experiments used antibody derivitized at a biotin:antibody ratio of 10:1.

TABLE 1

Effect of Lysine Biotinylation on Immunoreactivity

| Molar Offering | Measured Derivitization | Immunoassessment (%) | |
|---|---|---|---|
| (Biotins/Ab) | (Biotins/Ab) | ELISA | Cell Binding |
| 5:1 | 3.4 | 86 | |
| 10:1 | 8.5 | 73 | 100 |
| 13:1 | 11.1 | 69 | 102 |

TABLE 1-continued

Effect of Lysine Biotinylation on Immunoreactivity

| Molar Offering | Measured Derivitization | Immunoassessment (%) | |
|---|---|---|---|
| (Biotins/Ab) | (Biotins/Ab) | ELISA | Cell Binding |
| 20:1 | 13.4 | 36 | 106 |
| 40:1 | 23.1 | 27 | |

Alternatively, NR-LU-10 was biotinylated using thiol groups generated by reduction of cysteines. Derivitization of thiol groups was hypothesized to be less compromising to antibody immunoreactivity. NR-LU-10 was radioiodinated using p-aryltin phenylate NHS ester (PIP-NHS) and either $^{125}$I or $^{131}$I sodium iodide. Radioiodinated NR-LU-10 was incubated with 25 mM dithiothreitol and purified using size exclusion chromatography. The reduced antibody (containing free thiol groups) was then reacted with a 10- to 100-fold molar excess of N-iodoacetyl-n'-biotinyl hexylene diamine in phosphate-buffered saline (PBS), pH 7.5, containing 5% DMSO (v/v).

TABLE 2

Effect of Thiol Biotinylation on Immunoreactivity

| Molar Offering | Measured Derivitization | Immunoassessment (%) | |
|---|---|---|---|
| (Biotins/Ab) | (Biotins/Ab) | ELISA | Cell Binding |
| 10:1 | 4.7 | 114 | |
| 50:1 | 6.5 | 102 | 100 |
| 100:1 | 6.1 | 95 | 100 |

As shown in Table 2, at a 50:1 or greater biotin:antibody molar offering, only 6 biotins per antibody were incorporated. No significant impact on immunoreactivity was observed.

The lysine- and thiol-derivitized biotinylated antibodies ("antibody (lysine)" and "antibody (thiol)", respectively) were compared. Molecular sizing on size exclusion FPLC demonstrated that both biotinylation protocols yielded monomolecular (monomeric) IgGs. Biotinylated antibody (lysine) had an apparent molecular weight of 160 kD, while biotinylated antibody (thiol) had an apparent molecular weight of 180 kD. Reduction of endogenous sulfhydryls to thiol groups, followed by conjugation with biotin, may produce a somewhat unfolded macromolecule. If so, the antibody (thiol) may display a larger hydrodynamic radius and exhibit an apparent increase in molecular weight by chromatographic analysis. Both biotinylated antibody species exhibited 98% specific binding to immobilized avidin-agarose.

Further comparison of the biotinylated antibody species was performed using non-reducing SDS-PAGE, using a 4% stacking gel and a 5% resolving gel. Biotinylated samples were either radiolabeled or unlabeled and were combined with either radiolabeled or unlabeled avidin or streptavidin. Samples were not boiled prior to SDS-PAGE analysis. The native antibody and biotinylated antibody (lysine) showed similar migrations; the biotinylated antibody (thiol) produced two species in the 50–75 kD range. These species may represent two thiol-capped species. Under these SDS-PAGE conditions, radiolabeled streptavidin migrates as a 60 kD tetramer. When 400 µg/ml radiolabeled streptavidin was combined with 50 µg/ml biotinylated antibody (analogous to "sandwiching" conditions in vivo), both antibody species formed large molecular weight complexes. However, only the biotinylated antibody (thiol)-streptavidin complex moved from the stacking gel into the resolving gel, indicating a decreased molecular weight as compared to the biotinylated antibody (lysine)-streptavidin complex.

B. Blood Clearance of Biotinylated Antibody Species

Radioiodinated biotinylated NR-LU-10 (lysine or thiol) was intravenously administered to non-tumored nude mice at a dose of 100 µg. At 24 h post-administration of radio-iodinated biotinylated NR-LU-10, mice were intravenously injected with either saline or 400 µg of avidin. With saline administration, blood clearances for both biotinylated antibody species were biphasic and similar to the clearance of native NR-LU-10 antibody.

In the animals that received avidin intravenously at 24 h, the biotinylated antibody (lysine) was cleared (to a level of 5% of injected dose) within 15 min of avidin administration (avidin:biotin=10:1). With the biotinylated antibody (thiol), avidin administration (10:1 or 25:1) reduced the circulating antibody level to about 35% of injected dose after two hours. Residual radiolabeled antibody activity in the circulation after avidin administration was examined in vitro using immobilized biotin. This analysis revealed that 85% of the biotinylated antibody was complexed with avidin. These data suggest that the biotinylated antibody (thiol)-avidin complexes that were formed were insufficiently crosslinked to be cleared by the RES.

Blood clearance and biodistribution studies of biotinylated antibody (lysine) 2 h post-avidin or post-saline administration were performed. Avidin administration significantly reduced the level of biotinylated antibody in the blood, and increased the level of biotinylated antibody in the liver and spleen. Kidney levels of biotinylated antibody were similar.

C. Preparation of Biotinylated Antibody (Thiol) Through Endogenous Antibody Sulfhydryl Groups Or Sulfhydryl-Generating Compounds Certain antibodies have available for reaction endogenous sulfhydryl groups. If the antibody to be biotinylated contains endogenous sulfhydryl groups, such antibody is reacted with N-iodoacetyl-n'-biotinyl hexylene diamine. The availability of one or more endogenous sulfhydryl groups obviates the need to expose the antibody to a reducing agent, such as DTT, which can have other detrimental effects on the biotinylated antibody.

Alternatively, one or more sulfhydryl groups are attached to a targeting moiety through the use of chemical compounds or linkers that contain a terminal sulfhydryl group. An exemplary compound for this purpose is iminothiolane. As with endogenous sulfhydryl groups (discussed above), the detrimental effects of reducing agents on antibody are thereby avoided.

D. Targeting Moiety-Anti-Ligand Conjugate for Two-Step Pretargeting

1. Preparation of SMCC-derivitized streptavidin.

31 mg (0.48 µmol) streptavidin was dissolved in 9.0 ml PBS to prepare a final solution at 3.5 mg/ml. The pH of the solution was adjusted to 8.5 by addition of 0.9 ml of 0.5M borate buffer, pH 8.5. A DMSO solution of SMCC (3.5 mg/ml) was prepared, and 477 µl (4.8 µmol) of this solution was added dropwise to the vortexing protein solution. After 30 minutes of stirring, the solution was purified by G-25 (PD-10, Pharmacia, Piscataway, N.J.) column chromatography to remove unreacted or hydrolyzed SMCC. The purified SMCC-derivitized streptavidin was isolated (28 mg, 1.67 mg/ml).

2. Preparation of DTT-reduced NR-LU-10. To 77 mg NR-LU-10 (0.42 µmol) in 15.0 ml PBS was added 1.5 ml of 0.5M borate buffer, pH 8.5. A DTT solution, at 400 mg/ml (165 µl) was added to the protein solution. After stirring at room temperature for 30 minutes, the reduced antibody was purified by G-25 size exclusion chromatography. Purified DTT-reduced NR-LU-10 was obtained (74 mg, 2.17 mg/ml).

3. Conjugation of SMCC-streptavidin to EITT- reduced NR-LU-10. DTT-reduced NR-LU-10 (63 mg, 29 ml, 0.42 pmol) was diluted with 44.5 ml PBS. The solution of SMCC-streptavidin (28 mg, 17 ml, 0.42 µmol) was added rapidly to the stirring solution of NR-LU-10. Total protein concentration in the reaction mixture was 1.0 mg/ml. The progress of the reaction was monitored by HPLC (Zorbax® GF-250, available from MacMod). After approximately 45 minutes, the reaction was quenched by adding solid sodium tetrathionate to a final concentration of 5 mM.

4. Purification of conjugate. For small scale reactions, monosubstituted conjugate was obtained using HPLC Zorbax (preparative) size exclusion chromatography. The desired monosubstituted conjugate product eluted at 14.0–14.5 min (3.0 ml/min flow rate), while unreacted NR-LU-10 eluted at 14.5–15 min and unreacted derivitized streptavidin eluted at 19–20 min.

For larger scale conjugation reactions, monosubstituted adduct is isolatable using DEAE ion exchange chromatography. After concentration of the crude conjugate mixture, free streptavidin was removed therefrom by eluting the column with 2.5% xylitol in sodium borate buffer, pH 8.6. The bound unreacted antibody and desired conjugate were then sequentially eluted from the column using an increasing salt gradient in 20 mM diethanolaniine adjusted to pH 8.6 with sodium hydroxide.

5. Characterization of Conjugate.

a. HPLC size exclusion was conducted as described above with respect to small scale purification.

b. SDS-PAGE analysis was performed using 5% polyacrylamide gels under non-denaturing conditions. Conjugates to be evaluated were not boiled in sample buffer containing SDS to avoid dissociation of streptavidin into its 15 kD subunits. Two product bands were observed on the gel, which correspond to the mono- and di- substituted conjugates.

c. Immunoreactivity was assessed, for example, by competitive binding ELISA as compared to free antibody. Values obtained were within 10% of those for the free antibody.

d. Biotin binding capacity was assessed, for example, by titrating a known quantity of conjugate with p-[I-125]

iodobenzoylbiocytin. Saturation of the biotin binding sites was observed upon addition of 4 equivalents of the labeled biocytin.

e. In vivo studies are useful to characterize the reaction product, which studies include, for example, serum clearance profiles, ability of the conjugate to target antigen-positive tumors, tumor retention of the conjugate over time and the ability of a biotinylated molecule to bind streptavidin conjugate at the tumor. These data facilitate determination that the synthesis resulted in the formation of a 1:1 streptavidin-NR-LU-10 whole antibody conjugate that exhibits blood clearance properties similar to native NR-LU-10 whole antibody, and tumor uptake and retention properties at least equal to native NR-LU-10.

Figure 8:
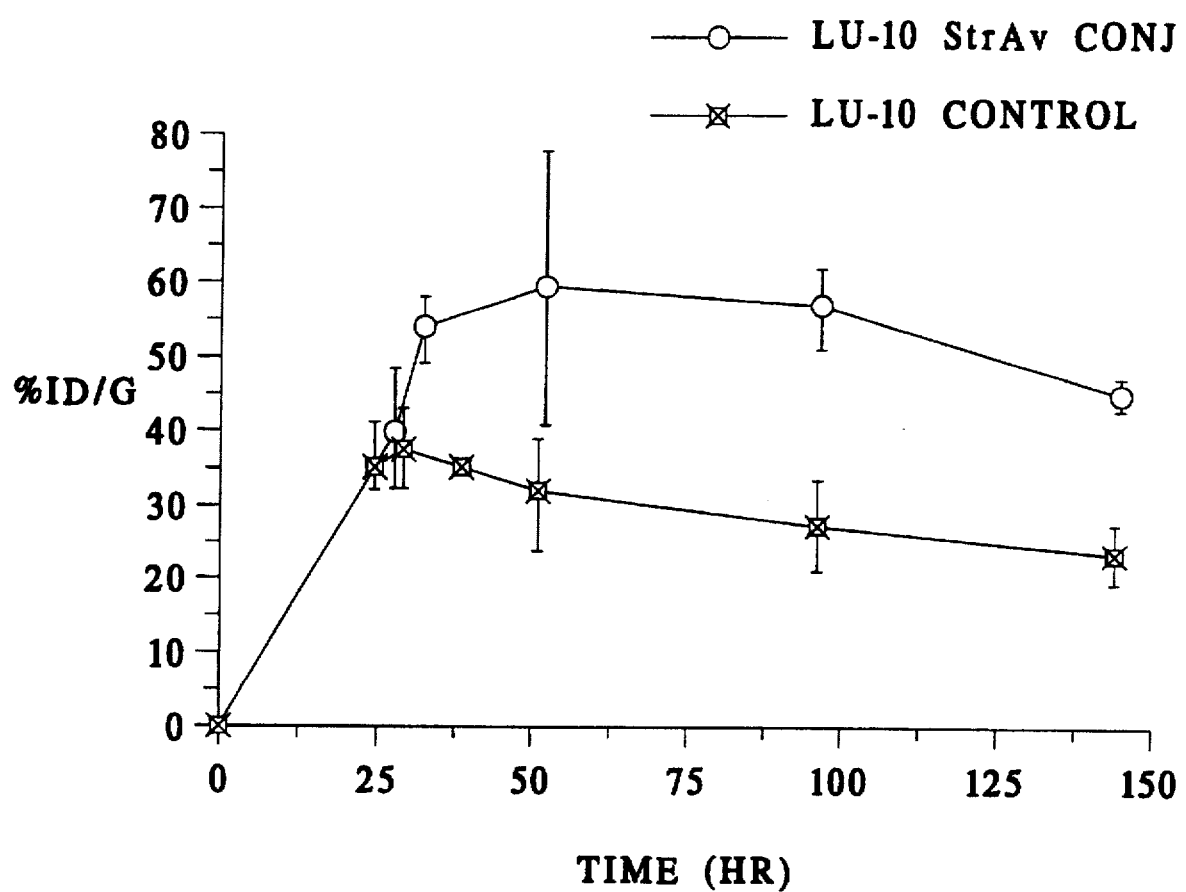
FIG. 8 depicts the tumor uptake profile of NR-LU-10 streptavidin conjugate (LU-10-StrAv) in comparison to a control profile of native NR-LU-10 whole antibody.

For example, FIG. 8 depicts the tumor uptake profile of the NR-LU-10-streptavidin conjugate (LU-10-StrAv) in comparison to a control profile of native NR-LU-10 whole antibody. LU-10-StrAv was radiolabeled on the streptavidin component only, giving a clear indication that LU-10-StrAv localizes to target cells as efficiently as NR-LU-10 whole antibody itself.

EXAMPLE XIV

Three-Step Pretargeting

A patient has ovarian cancer. A monoclonal antibody (MAb) directed to an ovarian cancer cell antigen is conjugated to biotin to form a MAb-biotin conjugate. The MAb-biotin conjugate is administered to the patient in an amount in excess of the maximum tolerated dose of conjugate administrable in a targeted, chelate labeled molecule protocol and is permitted to localize to target cancer cells for 24–48 hours. Next, an amount of avidin sufficient to clear non-targeted MAb-biotin conjugate and bind to the targeted biotin is administered. A biotin-radionuclide chelate conjugate of the type discussed in Example XII above is dispersed in a pharmaceutically acceptable diluent and administered to the patient in a therapeutically effective dose. The biotin-radionuclide chelate conjugate localizes to the targeted MAb-biotin-avidin moiety or is removed from the patient via the renal pathway.

EXAMPLE XV

Two-Step Pretargeting

A patient has colon cancer. A monoclonal antibody (MAb) directed to a colon cancer cell antigen is conjugated to streptavidin to form a MAb-streptavidin conjugate. The MAb-streptavidin conjugate is administered to the patient in an amount in excess of the maximum tolerated dose of conjugate administrable in a targeted, chelate labeled molecule protocol and is permitted to localize to target cancer cells for 24–48 hours. A biotin-radionuclide chelate conjugate of the type discussed in Example XII above is dispersed in a pharmaceutically acceptable diluent and administered to the patient in a therapeutically effective dose. The biotin-radionuclide chelate conjugate localizes to the targeted MAb-streptavidin moiety or is removed from the patient via the renal pathway.

EXAMPLE XVI

Glucose-Bearing Conjugates

A. Amide-linked Conjugate. The $N_2S_2$-biotin final product of Example XII(A) above has one free carboxyl group located on the chelating compound portion thereof. This carboxyl group is converted to a N-hydroxysuccinimidyl group using NHS and DCC in DMF. Side product DCU is removed by filtration. The filtrate is evaporated, and the residue NHS ester is used without further purification.

The residue is dissolved in DMF and three equivalents of triethylamine is added. To this solution is added glucosamine hydrochloride (commercially available from Aldrich Chemical Co., Milwaukee, Wis.). Progress of the reaction is monitored by thin layer chromatography (TLC). When TLC shows that the reaction is complete, the DMF and triethylamine are evaporated, and the product glucose-$N_2S_2$-biotin is purified by preparative reverse phase HPLC.

B. Multiple-glucose Conjugate. The $N_2S_2$-biotin final product of Example XII(B) above has two free carboxyl groups located on the chelating compound portion thereof. These carboxyl groups are free for reaction with a glucose-bearing moiety to form a glucose-bearing conjugate. The carboxyl groups are activated by conversion to N-hydroxysuccinimidyl esters using NHS and DCC in DMF. Side product DCU is removed by filtration. The filtrate is evaporated, and the residue bis-NHS ester is used without further purification.

The residue is dissolved in DMF containing six equivalents of triethylamine. To this solution is added two equivalents of glucosamine hydrochloride (commercially available from Aldrich Chemical Co., Milwaukee, Wis.). Progress of the reaction is monitored by TLC. When TLC shows that the reaction is complete, the DMF and triethylamine are evaporated, and the product glucose-$N_2S_2$-biotin is purified by preparative reverse phase HPLC.

C. Amine-bearing Chelating Compound-Biotin Conjugate Synthesis. An exemplary amine-bearing chelating compound synthesis proceeds through an epsilon-N-t-BOC-alpha-N-methyl-lysine intermediate. This intermediate is either commercially available or preparable in accordance with the following procedure.

1. Synthesis of epsilon-N-t-BOC-alpha-N-methyl lysine. Epsilon-N-t-BOC-lysine was mono-alpha-N-methylated by the following three step procedure. Epsilon-N-t-BOC-lysine was reacted with trifluoroacetic anhydride in THF. The trifluoroacetamide product was methylated by stirring a suspension of epsilon-N-t-BOC-alpha-N-TFA-lysine, sodium hydride and methyl iodide in DMF at room temperature for about 6 hours. Following isolation of epsilon-N-t-DOC-alpha-N-methyl-alpha-N-TFA-lysine by aqueous/organic extraction, the TFA group was cleaved by stirring a solution of the TFA-lysine derivative in a solution of 1:1 piperidine/THF at room temperature for about 4 hours.

2. Synthesis of alpha-N-methyl-alpha-N-biotinyl-L-lysine. The amino group is biotinylated by stirring the epsilon-N-t-BOC-alpha-N-methyl lysine with biotin-NHS ester in DMF at room temperature for 8 hours. The BOC group is cleaved by stirring a solution of epsilon-N-t-BOC-alpha-N-methyl-alpha-N-biotinyl lysine in trifluoroacetic acid at room temperature for about 1 hour to form alpha-N-methyl-alpha-N-biotinyl-L-lysine.

3. Synthesis of an $N_2S_2$ chelating compound bearing a protected lysine epsilon amino group and an activated ester reactive group. Epsilon-N-t-BOC-lysine and S-tetrahydropyranyl mercaptoacetic acid-N-hydroxysuccinimidyl ester (prepared in accordance with procedures set forth in U.S. Pat. No. 4,965,392, for example) are stirred at room temperature in DMF containing 2.0 equivalents triethylamine to give alpha-N-[S-tetrahydropyranylmercapto-acetyl]-epsilon-N-t-BOC-lysine. The free carboxyl group of this intermediate is activated by stirring with N-hydroxysuccinimide and DCC to give the N-hydroxysuccinimidyl ester. The NHS ester and S-acetamidomethylcysteine (commercially available from Bachem Calif., Torrence, Calif.) are condensed in DMF containing 2.0 equivalents triethylamine to give the diamide product, alpha-N-[S-tetrahydropyranylmercaptoacetyl]-epsilon-N-t-DOC-lysyl-S-acetamido methyl cysteine. The free carboxyl group of this intermediate is activated with NFS and DCC to give an activated NHS ester product.

4. Synthesis of amine-bearing chelating compound-biotin conjugate. The N-protected amine-bearing chelate compound activated ester formed in accordance with Subsection C3 of this Example is condensed with alpha-N-methyl-alpha-N-biotinyl-L-lysine formed in accordance with Subsection C2 of this example to give the N-protected chelating compound-biotin conjugate, alpha-N-[S-tetrahydropyranylmercaptoacetyl]-epsilon-N-t-BOC-lysyl-(S-acetamidomethyl)-cysteinyl-epsilon-N-[alpha-N-methyl-alpha-N-biotinyl]-lysine. The BOC protecting group of this intermediate is cleaved with formic acid to give the product, alpha-N-[S-tetrahydropyranylmercaptoacetyl]-lysyl-(S-acetamidomethyl)-cysteinyl-epsilon-N-(alpha-N-methyl-alpha-N-biotinyl)-lysine.

D. Amide-linked, Biotinylated, Sugar-derivatized Conjugate. The chelating compound prepared in accordance with the procedure described in Section C of this Example is conjugated to glucuronic acid (commercially available from Aldrich Chemical Co., Milwaukee, Wis.) using the water soluble coupling agent EDCI. A solution containing equimolar amounts of the chelating compound, glucuronic acid, EDCI and triethylamine in DMF is stirred for about 12 hours at room temperature, for example. The solvents are then evaporated. The product amine-linked conjugate is purified by reverse phase C-18 chromatography.

What is claimed is:

1. A compound of the formula:

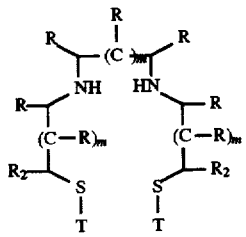

wherein:

each R independently represents =O, $H_2$, lower alkyl, —$(CH_2)_n$—COOH, —$(CH_2)_n$—CO-glucose or glucose derivative, —$(CH_2)_n$—NH-glucose or glucose derivative, or $R_1$—Z;

n is 0 to 3;

$R_1$ represents a lower alkyl or substituted lower alkyl group;

Z represents biotin or biotin with a linker moiety;

each $R_2$ independently represents $H_2$, a lower alkyl group, —$(CH_2)_n$—COOH, —$(CH_2)_n$—CO-glucose or glucose derivative, —$(CH_2)_n$—NH-glucose or glucose derivative, or $R_1$—Z;

each m is 0 or 1, wherein at most one m is m=1;

each T represents a sulfur protecting group; and the compound comprises at least one —$(CH_2)_n$—CO-glucose, —$(CH_2)_n$—NH-glucose or glucose derivative and at least one —$R_1$—Z substituent.

2. The compound of claim 1 wherein $R_1$ is a methylene chain comprising from two to three carbon atoms.

3. The compound of claim 1 wherein two R substituents are =O.

4. The compound of claim 1 wherein at least one $R_2$ substituent is —$(CH_2)_n$—COOH.

5. The compound of claim 1 wherein at least one T represents a hemithioacetal sulfur protecting group.

6. A compound of the formula:

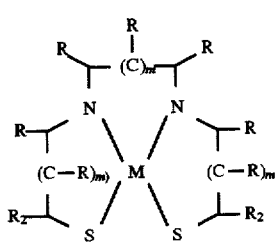

wherein:

M represents a radionuclide metal or an oxide thereof;

each R independently represents =O, $H_2$, lower alkyl, —$(CH_2)_n$—COOH, —$(CH_2)_n$—CO-glucose or glucose derivative, —$(CH_2)_n$—NH-glucose or glucose derivative, or $R_1$—Z;

n is 0 to 3;

$R_1$ represents a lower alkyl or substituted lower alkyl group;

Z represents a ligand or an anti-ligand or a ligand with a linker moiety or an anti-ligand with a linker moiety;

each $R_2$ independently represents $H_2$ lower alkyl, —$(CH_2)_n$—COOH, —$(CH_2)_n$—CO-glucose or glucose derivative, —$(CH_2)_n$—NH-glucose or glucose derivative, or $R_1$—Z;

each m is 0 or 1, wherein at most one m is m=1; and the compound comprises at least one —$(CH_2)_n$—CO-glucose, —$(CH_2)_n$—NH-glucose or glucose derivative substituent and at least one —$R_1$—Z substituent.

7. The compound of claim 6 wherein $R_1$ is a methylene chain comprising from two to three carbon atoms.

8. The compound of claim 6 wherein two R substituents are =O.

9. The compound of claim 6 wherein at least one $R_2$ substituent is —$(CH_2)_n$—COOH.

10. The compound of claim 6 wherein M represents a radionuclide metal selected from the group consisting of $^{99m}Tc$, $^{186}Re$, $^{188}Re$, and oxides thereof.

11. A compound of the formula:

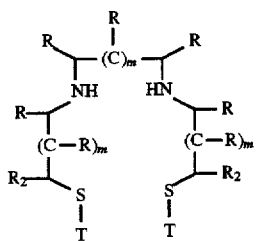

wherein:

each R independently represents =O, $H_2$, lower alkyl, —$(CH_2)_n$—COOH, —$(CH_2)_n$—CO-glucose or glucose derivative, —$(CH_2)_n$—NH-glucose or glucose derivative, or $R_1$—Z;

n is 0 to 3;

$R_1$ represents a lower alkyl or substituted lower alkyl group;

Z represents biotin or a biotin conjugation group or a biotin with a linker moiety;

each $R_2$ independently represents $H_2$, a lower alkyl group, —$(CH_2)_n$—COOH, —$(CH_2)_n$—CO-glucose or glucose derivative, —$(CH_2)_n$—NH-glucose or glucose derivative, or $R_1$—Z;

each m is 0 or 1, wherein at most one m is m=1;

each T represents a sulfur protecting group; and the compound comprises at least one —$(CH_2)_n$—COOH glucose, —$(CH_2)_n$—NH-glucose or glucose derivative and at least one —$R_1$—Z substituent.

12. A compound of the formula:

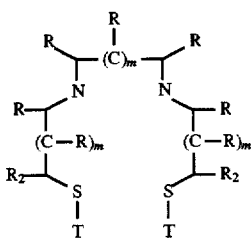

wherein:

each T represents a sulfur protecting group;

each R independently represents =O, $H_2$, lower alkyl, —$(CH_2)_n$—COOH, —$(CH_2)_n$—CO glucose or glucose derivative, —$(CH_2)_n$—NH-glucose or glucose derivative, or $R_1$—Z;

n is 0 to 3;

$R_1$ represents a lower alkyl or substituted lower alkyl group;

Z represents a ligand or an anti-ligand or a ligand with a linker moiety or an anti-ligand with a linker moiety;

each $R_2$ independently represents $H_2$ lower alkyl, —$(CH_2)_n$—COOH, —$(CH_2)_n$—CO-glucose or glucose derivative, —$(CH_2)_n$—NH-glucose or glucose derivative, or $R_1$—Z;

each m is 0 or 1, wherein at most one m is m=1; and the compound comprises at least one —$(CH_2)_n$—CO-glucose, —$(CH_2)_n$—NH-glucose or glucose derivative substituent and at least one —$R_1$—Z substituent.

13. A compound according to claim 1, additionally including M, wherein M represents a radionuclide metal or an oxide thereof.

* * * * *